United States Patent [19]

Girard et al.

[11] Patent Number: 5,530,017

[45] Date of Patent: Jun. 25, 1996

[54] METHOD OF ANTAGONIZING ANGIOTENSIN II RECEPTORS IN MAMMALS USING SUBSTITUTED [1H-IMIDAZOL-5-YL] ALKENOIC ACIDS

[75] Inventors: Gerald R. Girard, Bensalem, Pa.; Judith Hempel, Cardiff, Calif.; David T. Hill, North Wales, Pa.; James Samanen; Joseph Weinstock, both of Phoenixville, Pa.

[73] Assignee: SmithKline Beecham Corp, Philadelphia, Pa.

[21] Appl. No.: 433,001

[22] Filed: May 2, 1995

Related U.S. Application Data

[62] Division of Ser. No. 965,291, Jan. 29, 1993, Pat. No. 5,444,080, which is a continuation of Ser. No. 560,643, Jul. 31, 1990, abandoned.

[51] Int. Cl.$^6$ .................. A61K 31/415; C07D 233/64; C07D 233/68; C07D 233/84
[52] U.S. Cl. .................................................. 514/397
[58] Field of Search ............................. 514/397, 381, 514/399

[56] References Cited

U.S. PATENT DOCUMENTS

| | | | |
|---|---|---|---|
| 3,826,836 | 7/1974 | Buchel et al | 548/341.5 X |
| 4,340,598 | 7/1982 | Furukawa et al. | 548/341.5 X |
| 4,355,040 | 10/1982 | Furukawa et al. | 548/341.5 |
| 4,447,431 | 5/1984 | Sallmann | 548/341.5 X |
| 4,767,752 | 8/1988 | Ishii et al. | 548/341.5 X |

FOREIGN PATENT DOCUMENTS

| | | | |
|---|---|---|---|
| 0059156 | 9/1982 | European Pat. Off. | 548/341.5 |
| 0103647 | 3/1984 | European Pat. Off. | 548/341.5 |
| 0253310 | 1/1988 | European Pat. Off. | 548/341.5 |
| 0324377 | 7/1989 | European Pat. Off. | 548/341.5 |
| 0403158 | 12/1990 | European Pat. Off. | 548/341.5 |
| 0403159 | 12/1990 | European Pat. Off. | 548/341.5 |
| 0425211 | 5/1991 | European Pat. Off. | 548/341.5 |
| 0427463 | 5/1991 | European Pat. Off. | 548/341.5 |
| 0437103 | 7/1991 | European Pat. Off. | 548/341.5 |
| 57-98270 | 6/1982 | Japan | 548/341.5 |
| 63-270666 | 11/1988 | Japan | 548/341.5 |
| 63-303968 | 12/1988 | Japan | 548/341.5 |
| WO92/00068 | 1/1992 | WIPO | 548/341.5 |

*Primary Examiner*—Floyd D. Higel
*Attorney, Agent, or Firm*—Mary E. McCarthy; Stephen Venetianer; Edward T. Lentz

[57] ABSTRACT

Angiotensin II receptor antagonists having the formula:

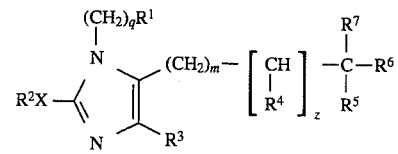

which are useful in regulating hypertension and in the treatment of congestive heart failure, renal failure, and glaucoma, pharmaceutical compositions including these antagonists, and methods of using these compounds to produce angiotensin II receptor antagonism in mammals.

7 Claims, No Drawings

METHOD OF ANTAGONIZING ANGIOTENSIN II RECEPTORS IN MAMMALS USING SUBSTITUTED [1H-IMIDAZOL-5-YL] ALKENOIC ACIDS

This application is a divisional of application Ser. No. 07/965,291, filed Jan. 29, 1993, now U.S. Pat. No. 5,444,080, which claims priority from PCT International Application No. PCT/U.S.91/05391, filed Jul. 30, 1991, which is a continuation of U.S. Ser. No. 07/560,643, filed Jul. 31, 1990, now abandoned.

The present invention relates to new substituted [imidazol-5-yl]alkanoic acids which are angiotensin II receptor antagonists and are useful in regulating hypertension induced or exacerbated by angiotensin II and in the treatment of congestive heart failure, renal failure, and glaucoma. This invention also relates to pharmaceutical compositions containing substituted [imidazol-5-yl]alkanoic acids and methods for using these compounds as antagonists of angiotensin II, as antihypertensive agents and as agents for treating congestive heart failure, renal failure, and glaucoma.

BACKGROUND OF THE INVENTION

The class of peptide pressor hormone known as angiotensin is responsible for a vasopressor action that is implicated in the etiology of hypertension in man. Inappropriate activity of the renin-angiotensin systems appears to be a key element in essential hypertension, congestive heart failure and in some forms of renal disease. In addition to a direct action on arteries and arterioles, angiotensin II (AII), being one of the most potent endogenous vasoconstrictors known, stimulates the release of aldosterone from the adrenal cortex. Therefore, the renin-angiotensin system, by virtue of its participation in the control of renal sodium handling, plays an important role in cardiovascular homostasis.

Interruption of the renin-angiotensin system with converting enzyme inhibitors, such as captopril, has proved to be clinically useful in the treatment of hypertension and congestive heart failure (Abrams, W. B., et al, (1984), *Federation Proc.*, 43, 1314). The most direct approach towards inhibition of the renin-angiotensin system would block the action of AII at the receptor. Compelling evidence suggests that AII also contributes to renal vasoconstriction and sodium retention that is characteristic of a number of disorders such as heart failure, cirrhosis and complications of pregnancy (Hollenberg, N. K., (1984), *J. Cardiovas. Pharmacol.*, 6, S176). In addition, recent animal studies suggest that inhibition of the renin-angiotensin system may be beneficial in halting or slowing the progression of chronic renal failure (Anderson, S., et al, (1985), *J. Clin. Invest.*, 76, 612). Also, a recent patent application (South African Patent Application Number 87/01,653) claims that AII antagonists are useful as agents for reducing and controlling elevated intraocular pressure, especially glaucoma, in mammals.

The compounds of this invention inhibit, block and antagonize the action of the hormone AII, and are therefore useful in regulating and moderating angiotensin-induced hypertension, congestive heart failure, renal failure, glaucoma, and other disorders attributed to the actions of AII. When compounds of this invention are administered to mammals, the elevated blood pressure due to AII is reduced, and other manifestations based on AII intercession are minimized and controlled. Compounds of this invention are also expected to inhibit diuretic activity.

Recognition of the importance of blocking and inhibiting the actions of AII has stimulated other efforts to synthesize antagonists of AII. The following references have disclosed imidazole derivatives which are described as having AII blocking activity and useful as hypotensive agents.

U.S. Pat. No. 4,340,598 discloses substituted imidazol-5-yl alkanoic acids, and amido and lower-alkyl ester derivatives thereof, of the formula:

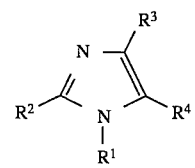

wherein $R^1$ is lower alkyl or phenyl$C_{1-2}$alkyl optionally substituted with halogen or nitro; $R^2$ is lower alkyl, cycloalkyl, or phenyl optionally substituted; one of $R^3$ and $R^4$ is -$(CH_2)_nCOR^5$, where $R^5$ is amino lower alkoxy or hydroxy and n is 0–2, and the other of $R^3$ and $R^4$ is hydrogen or halogen. Examples include 1-benzyl-2-n-butyl-4-chloroimidazole- 5-acetamide and 1-benzyl-2-n-butyl-5-chloroimidazole- 4-acetic acid.

U.S. Pat. No. 4,355,040 discloses substituted 1-benzylimidazol-5-yl acetic acid derivatives having the formula:

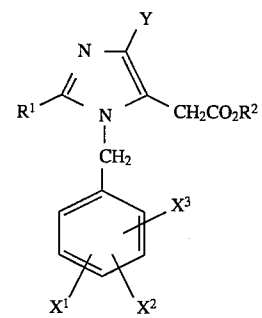

wherein $R^1$ is lower alkyl, cycloalkyl, or phenyl optionally substituted; $X^1$, $X^2$ and $X^3$ are each hydrogen halogen, nitro, amino, lower alkyl, lower alkoxy, benzyloxy, or hydroxy; Y is halogen and $R^2$ is hydrogen or lower alkyl. A compound specifically disclosed is 1-(2-chlorobenzyl)-2-n-butyl-4-chloro-imidazole- 5-acetic acid.

European Patent Application 103,647 discloses substituted 1-benzyl-2-phenyl-4-chloroimidazole-5-yl acetic acid derivatives of the formula:

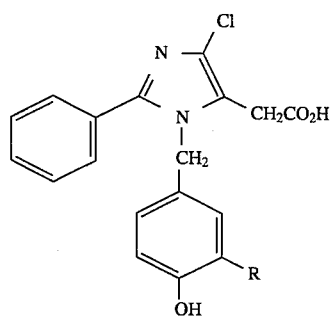

wherein R is lower alkyl. Specifically, the disclosure includes 4-chloro-1-(4-methoxy-3-methylbenzyl)-2-phenyl-imidazole- 5-acetic acid.

European Patent Application 253,310 discloses substituted 1-aralkylimidazoles having the general formula:

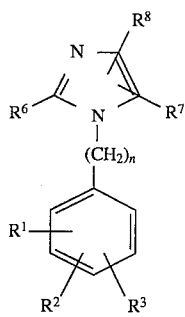

wherein $R^1$ includes groups such as phenyl optionally substituted or adamantylmethyl; $R^2$ includes groups such as hydrogen, halo, $NO_2$, $C_{1-4}$alkyl, or $C_{1-4}$alkoxy; $R^3$ is hydrogen, halo, $C_{1-4}$alkyl, or $C_{1-4}$alkoxy; $R^6$ includes groups such as $C_{2-10}$alkyl, $C_{3-10}$alkenyl, $C_{3-8}$cycloalkyl, benzyl optionally substituted or $Z(CH_2)_{1-5}$-$R^5$, wherein Z is O or S and $R^5$ is hydrogen, $C_{1-6}$alkyl, $C_{3-6}$cycloalkyl or alkenyl; $R^7$ is hydrogen, halo, $NO_2$, $CF_3$, or CN; and $R^8$ includes groups such as $C_{1-10}$alkanoic acids, esters and amides and alkyl N-alkyl carbamates. Examples include 2-n-butyl-5-chloro-1-(4-nitrobenzyl) imidazole-4-acetic acid and 1-[(2'-carboxybiphenyl- 4-yl)methyl]-2-n-butyl-4-chloro-5-(dimethylcarbamoyl)imidazole.

DESCRIPTION OF THE INVENTION

The compounds of the present invention that are blockers of angiotensin II receptors are represented by the following Formula (I):

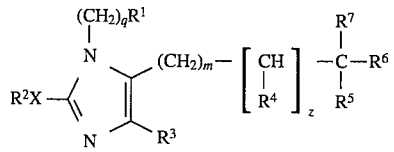

in which:

$R^1$ is adamantylmethyl, or phenyl, biphenyl, or naphthyl, with each aryl group being unsubstituted or substituted by one to three substituents selected from Cl, Br, F, I, $C_{1-6}$alkyl nitro, $CO_2R^8$, tetrazol-5-yl, $C_{1-6}$alkoxy, hydroxy, $SC_{1-4}$alkyl, $SO_2NHR^8$, $NHSO_2R^8$, $SO_3H$, $CONR^8R^8$, CN, $SO_2C_{1-4}$alkyl, or $C_nF_{2n+1}$, wherein n is 1–3;

$R^2$ is $C_{2-10}$alkyl, $C_{3-10}$alkenyl, $C_{3-10}$alkynyl, $C_{3-6}$cycloalkyl, or $(CH_2)_{0-8}$-phenyl unsubstituted or substituted by one to three substituents selected from $C_{1-6}$alkyl, nitro, Cl, Br, F, I, hydroxy, $C_{1-6}$alkoxy, $NR^8R^8$, $CO_2R^8$, CN, or $CONR^8R^8$;

X is a single bond, S, or O;

$R^3$ is hydrogen, Cl, Br, F, I, CHO, hydroxymethyl, $CO_2R^8$, $CONR^8R^8$, $NO_2$, or $C_nF_{2n+1}$, wherein n is 1–3;

q is 0 to 4;

m is 0 to 2;

$R^4$ is H or $C_{1-6}$alkyl;

z is 0 to 1;

$R^5$ is $C_{3-6}$alkyl, $C_{3-6}$alkenyl, phenyl-Y-, 2- or 3-thienyl-Y-, 2-or 3-furyl-Y-, 2-, 3-, or 4-pyridyl-Y-, tetrazolyl-Y-, triazolyl-Y-, imidazolyl-Y-, pyrazolyl-Y-, thiazolyl-Y-, pyrrolyl-Y-, or oxazolyl-Y-, with each aryl ring being unsubstitued or substitued by $C_{1-6}$alkyl, Cl, Br, F, I, $C_{1-6}$alkoxy, $NR^8R^8$, $CO_2R^8$, or $CONR^8R^8$;

Y is a single bond or $C_{1-6}$alkyl which is branched or unbranched;

$R^6$ is $CO_2R^8$, $CONR^8R^8$, or tetrazol-5-yl;

$R^7$ is H, $CO_2R^8$, or $C_{1-6}$alkyl; and each $R^8$ independently is hydrogen, $C_{1-6}$alkyl, or $(CH_2)_{0-4}$phenyl;

or a pharmaceutically acceptable salt thereof.

Preferred compounds of the invention are represented by Formula (I) when:

$R^1$ is phenyl unsubstituted or substituted by one to three substituents selected from chloro, fluoro, trifluoromethyl, nitro, methyl, methoxy, hydroxy, sulfonamido, cyano, carboxy, carbo$C_{1-6}$alkoxy, carbamoyl, or tetrazol-5-yl;

q is one;

X is a single bond or S;

$R^2$ is $C_2$-$C_8$alkyl;

$R^3$ is hydrogen, chloro, fluoro, or $C_nF_{2n+1}$, wherein n is 1–3; and $R^5$ is $C_{4-6}$alkyl, phenyl-$CH_2$-, or thienyl-$CH_2$-, with each aryl ring being unsubstituted or substituted by methyl, methoxy, or chloro; or a pharmaceutically acceptable salt thereof.

As used herein, the terms alkyl, alkenyl, alkoxy, and alkynyl mean carbon chains which are branched or unbranched with the length of the chain determined by the descriptor preceding the term. Included within the scope of Formula (I) compounds are the racemic mixtures as well as the single enantiomers encompassed by the genus of Formula (I).

Particular compounds of the invention include, but are not limited to, the following:

3-[2-n-butyl-1-{(4-carboxyphenyl)methyl}1H-imidazol-5-yl]-2-benzylpropanoic acid, 3-[2-n-butyl-1-{4-carboxyphenyl)methyl}-1H-imidazol-5-yl] -2-(2-thienylmethyl)propanoic acid, 3-[2-n-butyl-1-{(4-carboxyphenyl)methyl}-1H-imidazol-5-yl]-2-(4-chlorobenzyl)propanoic acid, 3-[2-n-butyl-1-{4-carboxyphenyl)methyl}-4-chloro-1H-imidazol- 5-yl]-2-(2-thienylmethyl)propanoic acid, 3-[2-n-butyl-1-{(2-chlorophenyl)methyl}-1H-imidazol-5-yl]-2-benzylpropanoic acid, 3-[2-n-butyl-1-{(2-chlorophenyl)methyl}-1H-imidazol-5-yl]-2-n-butylpropanoic acid, 3-[2-n-butyl-4-chloro-1-{(2-chlorophenyl)methyl}-1H-imidazol- 5-yl]-2-benzylpropanoic acid, (2RS,3SR)-3-[2-n-butyl-1-{(2-chlorophenyl)methyl}-1H-imidazol- 5-yl]-2-benzyl-3-methylpropanoic acid, 3-[2-n-butyl-1-benzyl-1H-imidazol-5-yl]-2-benzylpropanoic acid, 2-carboethoxy-3-[1-{(2-chlorophenyl)methyl}-2-propylthio- 1H-imidazol-5-yl]propanoic acid, 3-[1-{(2-chlorophenyl)methyl}-2-propylthio-1H-imidazol- 5-yl]-2-benzylpropanoic acid, 3-[1-{(2-chlorophenyl)methyl}-2-propylthio-1H-imidazol- 5-yl]-2-n-pentylpropanoic acid, 3-[1-{(2-chlorophenyl)methyl}-2-propylthio-1H-imidazol- 5-yl]-2-(2-propenyl)propionic acid, 2-[2-n-butyl-1-{(2-chlorophenyl)methyl}-1H-imidazol-5-yl]-2-benzylmalonic acid, methyl 3-[2-n-butyl-1-{(2-chlorophenyl)methyl}-1H-imidazol- 5-yl]-2-benzylpropionate, 3-[2-n-butyl-1-{(4-carboxyphenyl)methyl}-1H-imidazol-5-yl]-2-(2-thienylmethyl)propanoic acid, and 3-[2-n-butyl-1-{(4-carboxyphenyl)methyl}-1H-imidazol-5-yl]-2-benzylpropanoic acid; or a pharmaceutically acceptable salt thereof.

The invention also relates to pharmaceutical compositions comprising a pharmaceutical carrier and an effective amount of a compound of Formula (I).

Also included in the present invention are methods for antagonizing angiotensin II receptors which comprises administering to a subject in need thereof an effective amount of a compound of Formula (I). Methods of treating hypertension, congestive heart failure, renal failure, and glaucoma by administering these compounds are also included in this invention.

The compounds of this invention and of the pharmaceutical compositions and methods of this invention are prepared by procedures described herein and illustrated by the examples. Reagents, protecting groups and functionality on the imidazole and other fragments of the molecule must be consistent with the proposed chemical transformations. Steps in the synthesis must be compatible with the functional groups and the protecting groups on the imidazole and other parts of the molecule.

$CF_3$, $CO_2C_{1-6}alkyl$, $SC_{1-4}alkyl$, or $SO_2C_{1-4}alkyl$, are reacted with a thiocyanate, such as ammonium thiocyanate, in a suitable solvent, such as water, at a temperature of about 40° C. to about 100° C., preferably at about 80° C., to give formula (2) thiourea compounds. The free thio group of the formula (2) compounds is reacted with a halo-$R^9$ compound, wherein $R^9$ is $C_{2-10}alkyl$, $C_{3-10}alkenyl$, $C_{3-10}alkynyl$, $C_{3-6}cycloalkyl$, or an optionally substituted $(CH_2)_{0-8}phenyl$, preferably propylbromide, in a suitable solvent, such as acetonitrile, at a temperature of about 50° C. to about 80° C., preferably at about 80° C., to give formula (3) compounds. Formation of the imidazole nucleus is accomplished by reacting the formula (3) compounds with a $C_{1-6}alkyl$ 3-formyl-2-($R^5$-substituted)-2-propanoate of formula (4) which had been synthesized by reacting (triphenylphosphoranylidene)acetaldehyde with an $R^5$-CO-$CO_2C_{1-6}alkyl$ compound. These formula (5) ester imidazoles, which are Formula (I) compounds, are hydrolyzed to formula (6) acids using base, such as potassium, sodium, or lithium hydroxide, in a suitable solvent system, such as aqueous $C_{1-4}alkanols$ or diglyme, or aqueous acid, such as aqueous hydrochloric acid. Formula (6) compounds are Formula (I) compounds.

SCHEME I

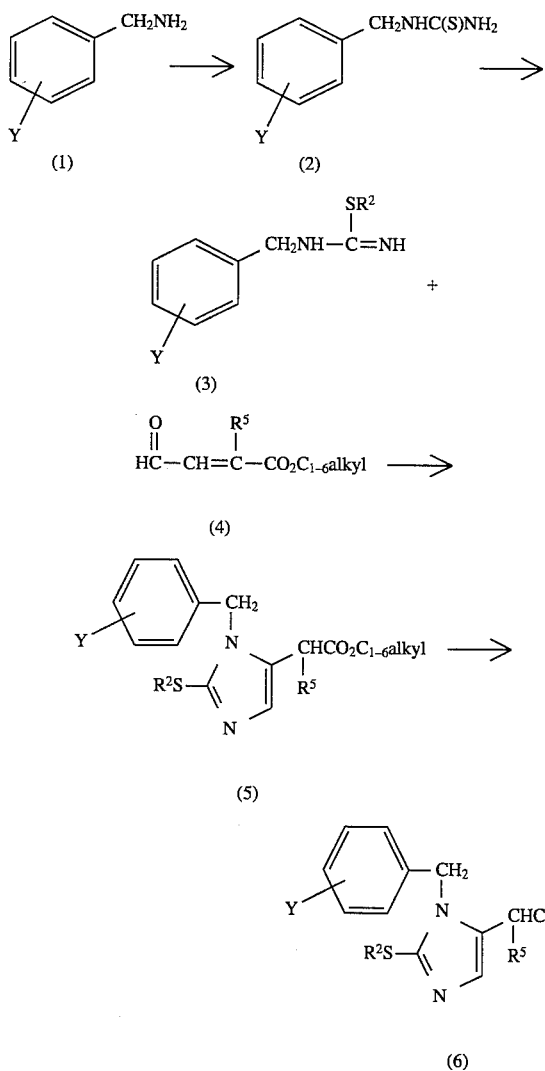

SCHEME II

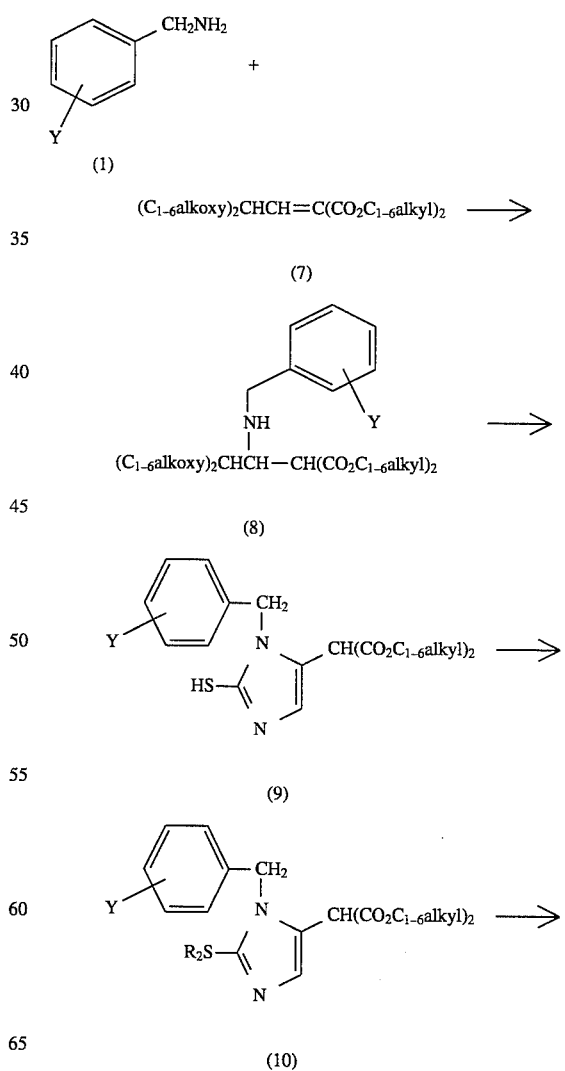

Scheme I shows the synthesis of Formula (I) compounds wherein X is S, $R^1$ is a phenyl unsubstituted or substituted by a group Y, hereinbelow defined, $R^2$ is as defined for Formula (I) compounds, $R^3$ is H, m and z are each 0, q is one, $R^7$ is hydrogen, and $R^6$ is $CO_2H$ or $CO_2C_{1-6}alkyl$. According to Scheme I, formula (1) benzylamines, which are unsubstituted or substituted by one to three Y substituents selected from halo, $C_{1-6}alkyl$, $C_{1-6}alkoxy$, CN, $NO_2$, -continued
SCHEME II

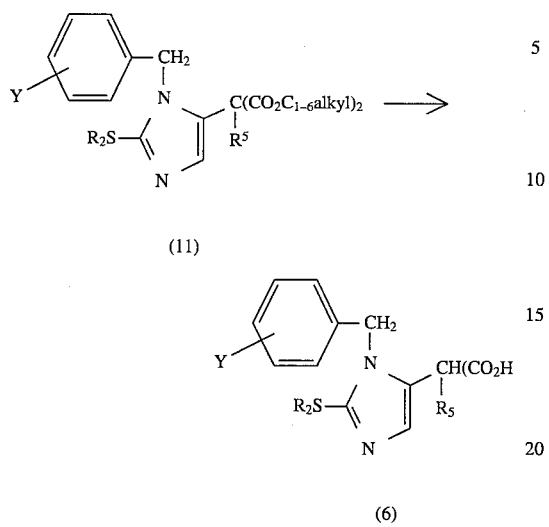

Scheme II shows an alternate synthesis of Scheme I, formula (6) compounds. According to Scheme II, Scheme I, formula (1) benzylamines are condensed with di-$C_{1-6}$alkyl 2,2-di-$C_{1-6}$alkoxyethylidene malonates of formula (7) in a suitable solvent, such as ethanol, to give formula (8) compounds. The formula (7) malonates are prepared by reacting di-$C_{1-6}$alkyl oxomalonates with (triphenyl-phosphoranylidene)acetaldehyde in a suitable solvent, such as toluene, followed by acetal formation with tri-$C_{1-6}$alkyl orthoformate in the presence of strong acid, such as p-toluenesulfonic acid, and a water-scavenging agent, such as 3A molecular sieves. Imidazole formation is accomplished by reaction of the formula (8) intermediates with a thiocyanate, such as potassium thiocyanate, in aqueous hydrochloric acid solution and an organic solvent, such as a $C_{1-4}$alkyl alcohol, to give formula (9) compounds. The free thio group of the formula (9) imidazoles is reacted with a halo-$R^9$ compound, wherein $R^9$ is as defined hereinabove, in a suitable solvent such as acetonitrile, at a temperature of about 50° C. to about 80° C., preferably at about 80° C., to give formula (10) compounds. The malonate compounds of formula (10) are alkylated with a $R^5$-halide, -acetate, or -sulfonate, such as benzyl bromide, in the presence of a suitable base, such as alkali metal alkoxide, for example, sodium ethoxide, in a suitable solvent, such as a $C_{1-4}$alkyl alcohol, to give formula (11) compounds. Hydrolysis and concomitant decarboxylation of the formula (11) malonates is carried out with aqueous base, for example, aqueous sodium carbonate solution, in a suitable solvent, such as a $C_{1-4}$alkyl alcohol at a temperature of about 60° C. to about 100° C., preferably at about 80° C. to give formula (6) acid compounds

SCHEME III

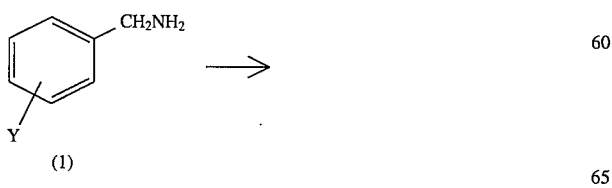

-continued
SCHEME III

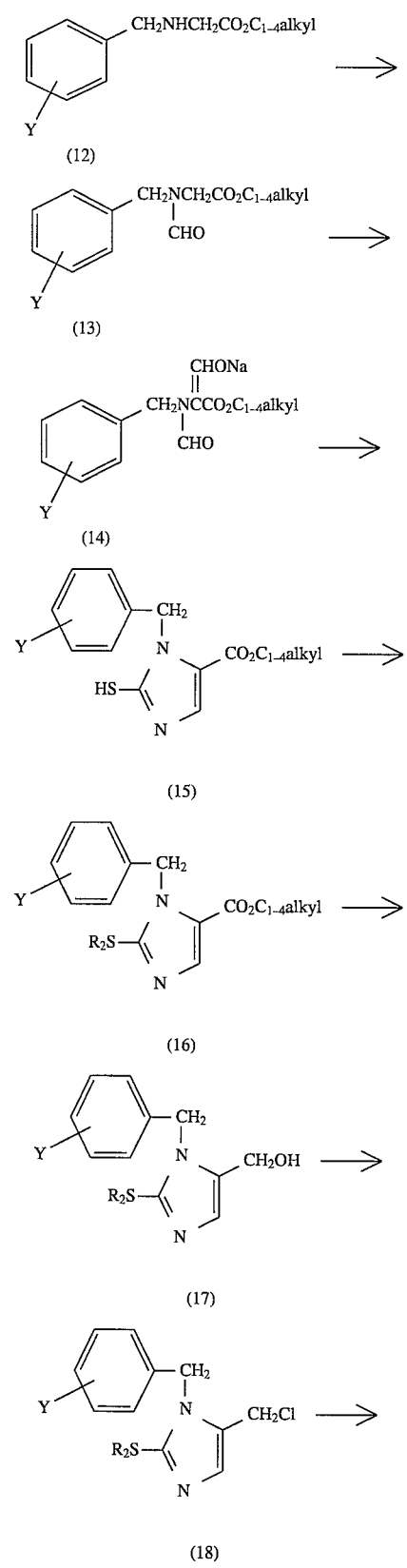

-continued
SCHEME III

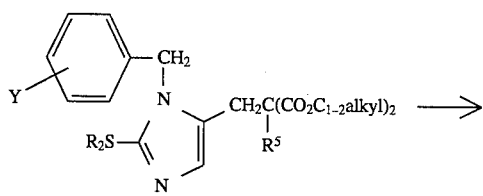

(19)

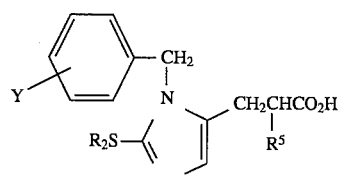

(20)

Scheme III outlines the synthesis of Formula (I) compounds in which the 2-position substituent is $R^2S$, m and q are 1, and z is 0. Formula (1) benzylamines, hereinbefore described, are alkylated with a $C_{1-4}$alkyl chloroacetate, for example, methyl chloroacetate, in the presence of a base, such as triethylamine, in a suitable solvent, such as dimethylformamide. The resulting alkylaminoalkyl ester compounds of formula (12) are N-formylated with formic acid in the presence of a suitable solvent, such as xylene, to give formula (13) compounds. Formula (14) compounds are formed by C-formylation of the carbon alpha to both the amino and the ester groups of the formula (13) compounds in a reaction with an alkyl formate, such as methyl formate, in the presence of an alkali metal halide, such as sodium hydride, in a suitable solvent, such as tetrahydrofuran. Reaction of this intermediate with a thiocyanate, preferably potassium thiocyanate in aqueous hydrochloric acid solution, and an organic solvent, such as $C_{1-4}$alkanol, produces 1-$R^1$$CH_2$-2-mercapto-5-alkanoate ester imidazoles (15). The free thio group of formula (15) compounds is reacted with a halo-$R^9$ compound, wherein $R^9$ is as described previously, in the presence of a suitable base, such as sodium carbonate, in an appropriate solvent, such as ethyl acetate, to give 1-$R^1$$CH_2$-2-$R^2$S-5-alkanoate ester imidazoles (16). The hydroxymethyl imidazoles of formula (17) are prepared from formula (16) compounds by reduction with an appropriate reagent, such as diisobutyl aluminum hydride, in a suitable solvent, such as tetrahydrofuran, at a temperature of about $-78°$ C. to about $25°$ C., preferably at about $-10°$ C. The formula (18) chloromethyl compounds are prepared by reacting formula (17) hydroxymethyl compounds with a halogenating agent, such as thionyl chloride. Reaction of formula (18) compounds with a di-$C_{1-2}$alkyl $R^5$-malonate, wherein $R^5$ is as defined for Formula (I), such as diethyl 2-thienylmethylmalonate, which had been pre-treated with a deprotonating agent, such as sodium hydride, yields formula (19) compounds. Optionally, formula (19) compounds, wherein $R^7$ is H, are alkylated with a $C_{1-4}$alkyl halide, such as methyl iodide, to give the formula (19) compounds, wherein $R^7$ is $C_{1-6}$alkyl. Formula (20) compounds, which are Formula (I) compounds, are prepared from formula (19) di-ester compounds using strong aqueous base, such as aqueous potassium hydroxide solution, in a suitable organic solvent, such as methanol or ethanol, at reflux temperatures.

Alternatively, formula (19) compounds are de-esterified and de-carboxylated in a stepwise fashion. For example, one of the ester groups of a formula (19) imidazole is removed using mild aqueous base, such as aqueous sodium bicarbonate solution, in a suitable organic solvent, such as methanol or ethanol, to give Formula (I) compounds, wherein one of $R^7$ or $R^6$ is $CO_2C_{1-6}$alkyl and the other is $CO_2H$. These half-acid, half-ester compounds are de-carboxylated, for example, by heating the compound neat at a temperature of about $120°$ C. to about $180°$ C., preferably at about $130°$ C. to about $170°$ C. Formula (20) compounds are prepared from this mono-ester intermediate using aqueous base, such as aqueous sodium or potassium hydroxide solution, in a suitable organic solvent, such as methanol or ethanol.

Formula (I) compounds wherein m is 2 are prepared using formula (10) imidazole compounds as intermediates. In this synthesis, hydrolysis/decarboxylation of the formula (10) compounds is carried as described for the conversion of formula (11) to formula (6) compounds. This acid is esterified using conventional techniques, for example, stirring the acid in methanol saturated with hydrochloric acid. Reduction of the ester to the 2-hydroxyethyl derivative is accomplished using a suitable hydride reagent, such as diisobutylaluminum hydride, in an inert organic solvent, such as tetrahydrofuran, at a temperature of about $-78°$ C. to about $25°$ C. Conversion to the chloroethyl imidazoles takes place by reacting the hydroxyethyl intermediates with a suitable halogenating agent, such as thionyl chloride. Formula (I) compounds wherein m is 2 are prepared as described in Scheme III, replacing formula (18) chloromethyl compounds with the above-prepared chloroethyl intermediates.

SCHEME IV

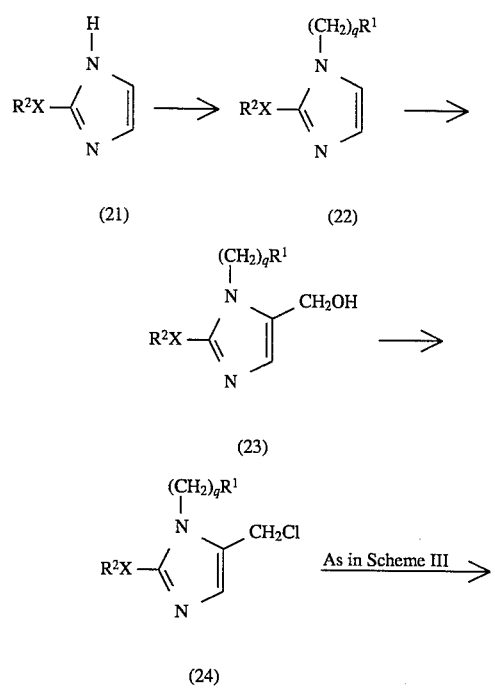

-continued
SCHEME IV

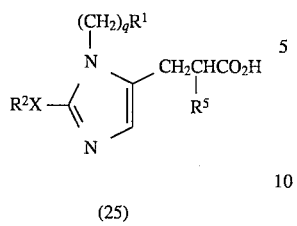

(25)

The starting materials, 2-R²X-imidazoles of formula (21) are known to the art (*J. Org. Chem.* 45:4038, 1980) or are synthesized by known procedures. For example, imidazole is converted to 2-n-butylimidazole by reacting imidazole with triethylorthoformate and p-toluenesulfonic acid to give 1-diethoxyorthoamide imidazole and then treating with n-butyl lithium to give the 2-lithium derivative of the orthoamide and alkylating with n-butyl iodide in a suitable solvent, such as tetrahydrofuran.

According to Scheme IV, the $1\text{-}R^1(CH_2)_q$-group is incorporated onto the 2-R²X-imidazole of formula (21) by known procedures, for example, by reaction with an $R^1\text{-}CH_2$ halide, mesylate or acetate, such as 2-chlorobenzyl bromide, in a suitable solvent, such as dimethylformamide, in the presence of suitable acid acceptor, such as sodium alkylate, potassium or sodium carbonate, or a metal hydride, preferably sodium hydride, at a reaction temperature of about 25° C. to about 100° C., preferably at about 50° C. The resulting $1\text{-}R^1(CH_2)_q\text{-}2\text{-}R^2X$-imidazole of formula (22) is hydroxymethylated in the 5-position, for example, by reacting with formaldehyde in the presence of sodium acetate in acetic acid to provide the $1\text{-}R^1(CH_2)_q\text{-}2\text{-}R^2X\text{-}5$-hydroxymethylimidazole intermediates of formula (23).

Alternatively, the $1\text{-}R^1(CH_2)_q\text{-}2\text{-}R^2X\text{-}5$- hydroxymethylimidazole intermediates are prepared by reacting an imido ether, $R^2X\text{-}C(=NH)\text{-}O\text{-}alkyl$, such as valeramidine methyl ether, with dihydroxyacetone in liquid ammonia under pressure to give 2-R²X-5-hydroxymethylimidazole. This intermediate is reacted with acetic anhydride to give 1-acetyl-5-acetoxymethyl- 2-R²X- imidazole. The diacetate intermediate is N-alkylated, for example, using 2-chlorobenzyl triflate, and the resulting $1\text{-}R^1(CH_2)_q\text{-}2\text{-}R^2X\text{-}5$-acetoxymethylimidazole is treated with aqueous base, such as 10% sodium hydroxide solution, to give the $1\text{-}R^1(CH_2)_q\text{-}2\text{-}R^2X\text{-}5$-hydroxymethylimidazole intermediate of formula (23).

The formula (23) hydroxymethyl compounds are converted to the corresponding chloromethyl compounds of formula (24) using a halogenating agent, such as thionyl chloride. Formula (I) compounds of formula (25) are prepared from formula (24) imidazoles following the procedures described in Scheme III, replacing formula (18) chloromethyl compounds with formula (24) chloromethyl imidazoles.

SCHEME V

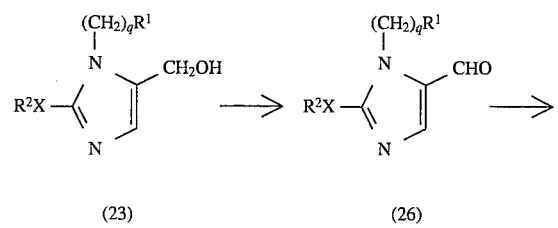

(23)                    (26)

(27)

(28)

(29)

Scheme V shows an alternate synthesis for the preparation of Formula (I) compounds wherein z is 0, m is 1, $R^6$ is $CO_2R^8$, and $R^1$, $R^2$, X, $R^5$, $R^8$, and q are as defined in Formula (I). According to Scheme V, the hydroxymethyl group of the Scheme IV formula (23) intermediate is oxidized to an aldehyde by treatment with a suitable reagent, such as anhydrous chromic acid-silica gel in tetrahydrofuran or, preferably, with activated maganese dioxide, in a suitable solvent, such as benzene or toluene, or preferably methylene chloride, at a temperature of about 25° C. to about 140° C., preferably at about 25° C., to give formula (26) compounds. These $1\text{-}R^1(CH_2)_q\text{-}2\text{-}R^2X$-imidazol-5-carboxaldehydes are reacted with an appropriate phosphonate, such as diethyl 2-n-butyl-2-phosphonopropionate. The phosphonates are prepared, for example, from trialkyl phosphonoacetates by alkylation with an appropriate halide, mesylate, or acetate in the presence of a suitable base, such as sodium hydride, in a suitable solvent, preferably glyme, at a reaction temperature of about 25° C. to about 110° C., preferably at about 55° C. The reaction of the imidazol-5-carboxaldehydes with the phosphonates is performed in the presence of a suitable base, such as a metal alkoxide, lithium hydride or preferably sodium hydride, in a suitable solvent, such as ethanol, methanol, ether, dioxane, tetrahydrofuran, or preferably glyme, at a reaction temperature of about 10° C. to about 50° C., preferably at about 25° C., to provide a variable mixture of trans and cis, e.g., (E) and (Z), $1\text{-}R^1(CH_2)_q\text{-}2\text{-}R^2X\text{-}5\text{-}CH=C(R^5)\text{-}(COOalkyl)$-imidazoles of formula (27). Reduction of the vinyl group of formula (27) compounds is accomplished using, for example, hydrogen in the presence of a catalyst, such as platinum oxide or palladium on carbon, in a suitable solvent, such as ethanol, to give formula (28) compounds. The formula (28) esters are hydrolyzed to the acids of formula (29) using base, such as potassium hydroxide, lithium hydroxide or sodiumhydroxide, in a suitable solvent system, such as aqueous alcohols or glyme.

Alternately, Formula (I) compounds are prepared from Scheme V, formula (26), compounds. The formula (26) aldehydes are reacted with a di-$C_{1-2}$alkyl malonate, such as diethyl malonate, in the presence of a base, such as piperidine. The resulting vinyl diester compounds are reduced to the corresponding saturated analogs using, for example, sodium borohydride in an appropriate solvent, such as ethanol. Reaction of this intermediate with a base, such as sodium hydride, followed by reaction with an $R^5$-halide, such as 4-chlorobenzyl chloride, yields formula (19)-type compounds. Formula (I) compounds are prepared by subsequent hydrolysis/decarboxylation as described hereinbefore.

Formula (I) compounds wherein $R^4$ is $C_{1-6}$alkyl are prepared by the following procedure. The 1-$R^1(CH_2)_q$-2-$R^2X$-imidazol- 5-carboxaldehydes, prepared as described above, are converted to the corresponding alcohols with an organometallic derivative or Grignard reagent, preferably methyl lithium, in a suitable solvent, such as tetrahydrofuran. The alcohol is oxidized, for example, using maganese dioxide to give the ketone. The olefinic esters are prepared from the ketone by reaction with appropriate phosphonates to give the (E) and/or (Z) isomers. The saturated acid compounds are prepared from the esters by catalytic hydrogenation and alkaline hydrolysis as described previously.

Alternatively, the 1-$R^1(CH_2)_q$-2-$R^2X$-imidazol-5 -carboxaldehydes of formula (26) are prepared by the following procedure. Starting 2-$R^2X$-imidazol-5-carboxaldehydes are reacted with an N-alkylating protecting reagent, such as chloromethyl pivalate (POM-Cl), in the presence of a base, such as potassium carbonate, in a suitable solvent, such as dimethylformamide, at a temperature of about 20° C. to about 50° C., preferably at about 25° C., to give N-alkylation (e.g., POM-derivation) on the least hindered nitrogen atom of the imidazole nucleus. The 1-$R^1(CH_2)_q$-group is incorporated onto the imidazole with an appropriately substituted halide compound, such as methyl 4-bromomethyl-3-chlorobenzoate, at a temperature of about 80° C. to about 125° C., preferably at about 100° C. The protecting group on the 3-nitrogen of the imidazole ring is removed by base hydrolysis, for example, using a biphasic mixture of ethyl acetate and aqueous sodium carbonate, to give 1-$R^1(CH_2)_q$-2-$R^2X$-imidazole-5-carboxaldehyde compounds. The Formula (I) compounds can be prepared from these 5-carboxaldehyde compounds by the methods described above.

SCHEME VI

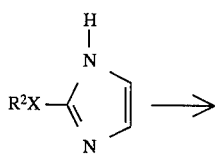

(21)

-continued
SCHEME VI

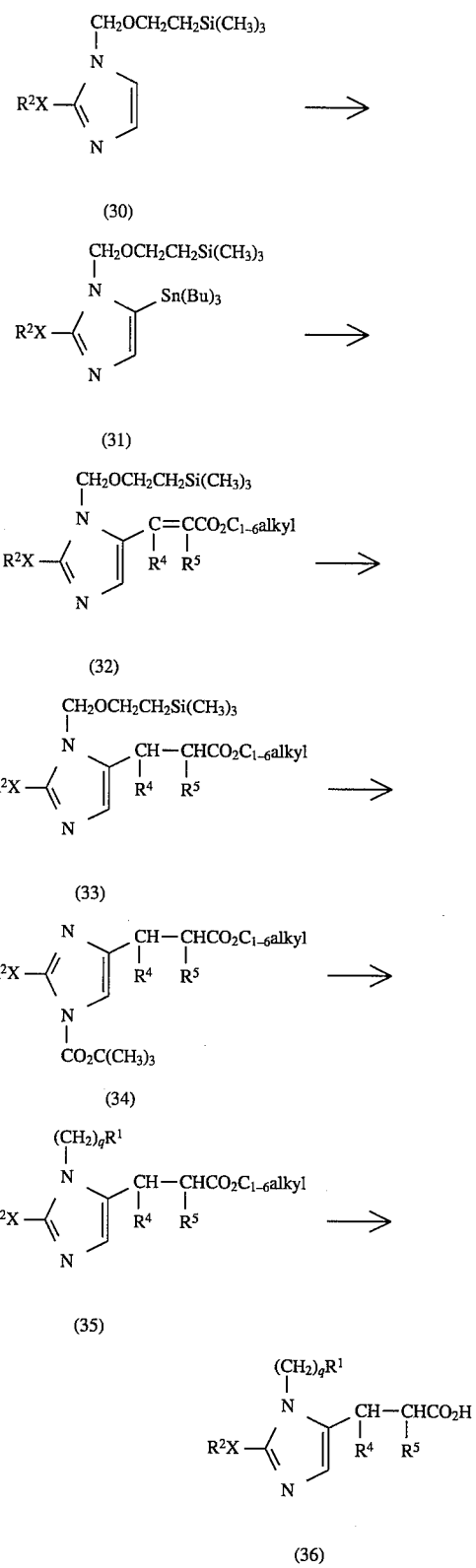

Scheme VI shows the synthesis of Formula (I) compounds wherein z is 1, m is 0 $R^6$ is $CO_2R^8$ and $R^1$, $R^2$, X, $R^4$, $R^5$, $R^8$, and q are as defined in Formula (I). According to Scheme VI, the 2-$R^2X$-imidazole starting materials of formula (21) are reacted with trimethylsilylethoxymethyl (SEM) chloride to give formula (30) 1-(trimethylsilyl)ethoxymethyl-2-$R^2$X-imidazole. The reaction is carried out, for example, in the presence of sodium hydride in a solvent, such as dimethylformamide. The formula (31) 5-tributyltin derivatives are prepared by lithiation with, for example, butyllithium in a suitable solvent, preferably diethyl ether, followed by treatment of the lithio imidazole derivative with a tributyltin halide, preferably tributyltin chloride, at about −10° C. to about 35° C., preferably at about 25° C. The 1-SEM-2-$R^2$X-5-tributyltinimidazole of formula (31) is coupled with an a,b-unsaturated acid ester having a leaving group on the b-position, such as a halide or trifluoromethane-sulfonyloxy group, for example, $BrCR^4=C(R^5)(COOalkyl)$, in the presence of a phosphine ligand, such as bis(diphenylphosphino)propane or triphenylphosphine and a palladium (II) compound, or preferably tetrakis(triphenylphosphine)-palladium(O), with or without a base, such as tributylamine, at a temperature of about 50° C. to about 150° C., preferably at about 120° C., to give formula (32) compounds. Reduction of vinyl group of formula (32) compounds is accomplished using, for example, hydrogen in the presence of a catalyst, such as platinum oxide or palladium on carbon, in a suitable solvent, such as ethanol, to give formula (33) compounds. The 1-SEM group of the formula (33) imidazoles is hydrolyzed with acid, for example, aqueous hydrochloric acid, in a suitable alcoholic solvent, such as methanol or ethanol. The 1-unsubstituted imidazole derivatives are converted to the 1-t-butoxycarbonyl (t-BOC) imidazoles with di-t-butyl dicarbonate (Hoppe-Seyler's *Z. Physiol. Chem.*, (1976) 357, 1651) to give formula (34) compounds The t-BOC esters are alkylated and hydrolyzed with, for example, 2-chlorobenzyl-O-triflate, in a suitable solvent, preferably methylene chloride, to afford the 1-$R^1$-$(CH_2)_q$-imidazote derivatives (esters) of formula (35). The formula (36) acid compounds are prepared from formula (35) esters using base hydrolysis as described previously.

Alternately, Formula (I) compounds wherein the alkylene bridge at the 5-position of the imidazole ring is defined as m equal to 0–2 are prepared from the alkanoic acid ester compounds described in U.S. Pat. No. 4,340,598. These esters are reduced to the corresponding alcohols using a suitable reagent such as diisobutyl aluminum hydride, in an appropriate solvent, such as tetrahydrofuran, at a temperature of about −78° C. to about 25° C., preferably at less than about −10° C. Formula (I) compounds are prepared from the resulting alcohol compounds following the procedures described in Scheme III (17–20).

Compounds of Formula (I) in which the $R^1$ substituent is substituted by hydroxy are formed from Formula (I) compounds in which the $R^1$ group is substituted by $C_1$-$C_4$alkoxy using an ether-cleaving reagent, such as boron tribromide or hydrobromic acid.

Compounds of Formula (I) in which the $R^1$ substituent is substituted by carboxy are formed from Formula (I) compounds in which the $R^1$ group is substituted by $CO_2C_1$-$C_4$alkyl using basic hydrolysis, such as aqueous sodium or potassium hydroxide, in methanol or ethanol, or using acidic hydrolysis, such as aqueous hydrochloric acid.

Compounds of Formula (I) in which the $R^1$ substituent is substituted by a tetrazol-5-yl group are prepared from the corresponding carboxy compounds. For example, Formula (I) acid compounds are reacted with a halogenating agent, such as thionyl chloride, in a suitable solvent, for example benzene, to give the corresponding acid halide compounds. The acid halides are then converted to primary amide compounds in a reaction with concentrated ammonia. Subsequent dehydration of the amides with oxalyl chloride/dimethylformamide in acetonitrile/dimethylformamide yields the nitrile compounds, which are the immediate precursors to the Formula (I) tetrazole compounds. Tetrazole formation is accomplished by reacting the nitriles with azide, preferably aluminum azide prepared in situ by the reaction of sodium azide with aluminum chloride, in a suitable solvent, for example tetrahydrofuran. The Formula (I) compounds in which $R^6$ is $CO_2H$ are prepared from these Formula (I) tetrazole ester compounds by basic hydrolysis as described above.

Compounds of Formula (I) in which $R^6$ is tetrazol-5-yl are prepared from the corresponding carboxy compounds using the procedure hereinbefore described.

Pharmaceutically acceptable acid addition salts of compounds of Formula (I) are formed with appropriate organic or inorganic acids by methods known in the art. For example, the base is reacted with a suitable inorganic or organic acid in an aqueous miscible solvent such as ethanol, with the salt being isolated by removing the solvent or in an aqueous immiscible solvent, when the acid is soluble therein, such as ethyl ether or chloroform, with the desired salt separating directly or isolated by removing the solvent. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfonic, phosphoric and nitric acids.

Pharmaceutically acceptable base addition salts of compounds of Formula (I) which have an acidic group are prepared by known methods from organic and inorganic bases, including nontoxic alkali metal and alkaline earth bases, for example, calcium, lithium, sodium, and potassium hydroxide; ammonium hydroxide, and nontoxic organic bases, such as triethylamine, butylamine, piperazine, meglumine, choline, diethanolamine, and tromethamine.

Angiotensin II antagonist activity of the compounds of Formula (I) is assessed by in vitro and in vivo methods. In vitro antagonist activity is determined by the ability of the compounds to compete with $^{125}$I-angiotensin II for binding to vascular angiotensin II receptors and by their ability to antagonize the contractile response to angiotensin II in the isolated rabbit aorta. In vivo activity is evaluated by the efficacy of the compounds to inhibit the pressor response to exogenous angiotensin II in conscious rats and to lower blood pressure in a rat model of renin dependent hypertension.

Binding

The radioligand binding assay is a modification of a method previously described in detail (Gunther et al., Circ. Res. 47:278, 1980). A particular fraction from rat mesenteric arteries is incubated in Tris buffer with 80 pM of $^{125}$I-angiotensin II with or without angiotensin II antagonists for 1 hour at 25° C. The incubation is terminated by rapid filtration and receptor bound $^{125}$I-angiotensin II trapped on the filter is quantitated with a gamma counter. The potency of angiotensin II antagonists is expressed as the $IC_{50}$ which is the concentration of antagonist needed to displace 50% of the total specifically bound angiotensin II.

Aorta

The ability of the compounds to antagonize angiotensin II induced vasoconstriction is examined in the rabbit aorta.

Ring segments are cut from the rabbit thoracic aorta and suspended in organ baths containing physiological salt solution. The ring segments are mounted over metal supports and attached to force displacement transducers which are connected to a recorder. Cumulative concentration response curves to angiotensin II are performed in the absence of antagonist or following a 30-minute incubation with antagonist. Antagonist disassociation constants ($K_B$) of compounds of the invention are then calculated.

Inhibition of pressor response to angiotensin II in conscious rats

Rats are prepared with indwelling femoral arterial and venous catheters and a stomach tube (Gellai et al., Kidney Int. 15:419, 1979). Two to three days following surgery the rats are placed in a restrainer and blood pressure is continuously monitored from the arterial catheter with a pressure transducer and recorded on a polygraph. The change in mean arterial pressure in response to intravenous injections of 250 mg/kg angiotensin II is compared at various time points prior to and following the administration of the compounds intravenously or orally at doses of 3 to 300 mg/kg. The dose of compound needed to produce 50% inhibition of the control response to angiotensin II ($IC_{50}$) is used to estimate the potency of the compounds.

Antihypertensive activity

The antihypertensive activity of the compounds is measured by their ability to reduce mean arterial pressure in conscious rats made renin-dependent hypertensive by ligation of the left renal artery (Cangiano et al., J. Pharmacol. Exp. Ther. 208:310, 1979). Renal artery ligated rats are prepared with indwelling catheters as described above. Seven to eight days following renal artery ligation, the time at which plasma renin levels are highest, the conscious rats are placed in restrainers and mean arterial pressure is continuously recorded prior to and following the administration of the compounds intravenously or orally.

The intraocular pressure lowering effects employed in this invention may be measured by the procedure described by Watkins, et al., *J. Ocular Pharmacol.*, 1 (2):161–168 (1985).

The compounds of Formula (I) are incorporated into convenient dosage forms, such as injectable preparations, or for orally active compounds, capsules or tablets. Solid or liquid pharmaceutical carriers are employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies but, preferably, will be from about 25 mg to about 1 g per dosage unit. When a liquid carrier is used, the preparation will be in the form of a syrup, elixir, emulsion, soft gelatin capsule, sterile injectable liquid, such as an ampoule, or an aqueous or nonaqueous liquid suspension.

For topical ophthalmologic administration, the pharmaceutical compositions adapted include solutions, suspensions, ointments, and solid inserts. Typical pharmaceutically acceptable carriers are, for example, water, mixtures of water and water-miscible solvents such as lower alkanols or vegetable oils, and water soluble ophthalmologically acceptable non-toxic polymers, for example, cellulose derivatives such as methyl cellulose. The pharmaceutical preparation may also contain non-toxic auxiliary substances such as emulsifying, preserving, wetting, and bodying agents, as for example, polyethylene glycols; antibacterial components, such as quarternary ammonium compounds; buffering ingredients, such as alkali metal chloride; antioxidants, such as sodium metabisulfite; and other conventional ingredients, such as sorbitan monolaurate.

Additionally, suitable ophthalmic vehicles may be used as carrier media for the present purpose including conventional phosphate buffer vehicle systems.

The pharmaceutical preparation may also be in the form of a solid insert. For example, one may use a solid water soluble polymer as the carrier for the medicament. Solid water insoluble inserts, such as those prepared from ethylene vinyl acetate copolymer, may also be utilized.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral, parenteral, or topical products.

Doses of the compounds of Formula (I) in a pharmaceutical dosage unit as described above will be an efficacious, nontoxic quantity selected from the range of 0.01–200 mg/kg of active compound, preferably 1–100 mg/kg. The selected dose is administered to a human patient in need of angiotensin II receptor antagonism from 1–6 times daily, orally, rectally, topically, by injection, or continuously by infusion. Oral dosage units for human administration preferably contain from 1 to 500 mg of active compound. Lower dosages are used generally for parenteral administration. Oral administration, is used when safe, effective and convenient for the patient. Topical formulations contain the active compound in an amount selected from 0.0001 to 0.1 (w/v %), preferably from 0.0001 to 0.01. As a topical dosage unit form, an amount of active compound from between 50 ng to 0.05 mg, preferably 50 ng to 5 µg, is applied to the human eye.

The method of this invention of antagonizing angiotensin II receptors in mammals, including humans, comprises administering to a subject in need of such antagonism an effective amount of a compound of Formula (I). The method of this invention of producing antihypertensive activity and the method of treating congestive heart failure, glaucoma, and renal failure comprise administering a compound of Formula (I) to a subject in need thereof an effective amount to produce said activity.

The following examples illustrate preparation of compounds and pharmaceutical compositions of this invention. The examples are not intended to limit the scope of this invention as defined hereinabove and as claimed below.

EXAMPLE 1

2-[1-{(2-Chlorophenyl)methyl}-2-propylthio-1H-imidazol-5-yl]propionic Acid (i) ethyl 3-formyl-2-methyl-2-propanoate A solution of triphenylphosphoranylidene acetaldehyde (15.74 g, 0.0517 mol) in dry toluene (80 mL) was added all at once to ethyl pyruvate (5.65 mL, 0.0517 mol). The solution was heated at 95° C. for 1 hour and then concentrated to a syrup. Molecular distillation provided 2.1 g (29%) of the yellow, oily ethyl 3-formyl-2-methyl-2-propanoate.

(ii) 1-(2-chlorophenyl)methyl-2-propyl-2-thiopseudourea

A solution of 2-chlorobenzylamine hydrochloride (41 g, 0.23 mol) and ammonium thiocyanate (19.28 g, 0.253 mol) in water (170 mL) was heated on the steam bath for 18 hours. This mixture was concentrated in vacuo, and the residue was taken up in toluene (1 L) and azeotroped with a Dean-Stark head. The residue was triturated with wet diethyl ether to provide 27.6 g (60%) of 1-(2-chlorophenyl)methyl thiourea. The product was recrystallized from ethanol; mp 120°–122° C.

A mixture of 1-(2-chlorophenyl)methyl thiourea (3 g, 14.9 mmol) and propylbromide (13.5 g, 110 mmol) in acetonitrile (20 mL) was refluxed for 5 hours. The solvent was evaporated, the residue was dissolved in 200 mL of 50% water/ether and acidified with 48% hydrobromic acid solution. The two phases were separated, the aqueous layer was washed with ether and then the aqueous layer was basified with 10% sodium carbonate solution. The liberated product was extracted with diethyl ether, washed with water and brine, dried and concentrated to give 1-(2-chlorophenyl)methyl-2-propyl- 2-thiopseudourea (2.82 g, 78%); mp 112°–114° C.

(iii) ethyl 2-[1-{(2-chlorophenyl)methyl}-2-propylthio-1H-imidazol-5-yl]propionate A solution of 1-(2-chlorophenyl)methyl-2-propyl-2-thiopseudourea (3.42 g, 14 mmol) and ethyl 3-formyl-2-methyl- 2-propanoate (2 g, 14 mmol) in ethanol (15 mL) was refluxed for 5 hours and then concentrated in vacuo. The crude product (5.2 g) was dissolved in ether and extracted with 2N aqueous hydrochloric acid solution (4x). The aqueous acid extracts were washed with diethyl ether, and adjusted to pH 8.5 with solid sodium carbonate. The aqueous layer was extracted with ether and then dried over anhydrous sodium sulfate. The ether layer was concentrated to give 1.9 g (37%) of an amber syrup. This was flash chromatographed over silica gel with 3:2 cyclohexane/ethyl acetate to afford 0.75 g of ethyl 2-[1-{(2-chlorophenyl)methyl}-2-propylthio-1H-imidazol- 5-yl]propionate as an oil.

(iv) 2-[1-{(2-chlorophenyl)methyl}-2-propylthio-1H-imidazol- 5-yl]propionic acid A solution of ethyl 2-[1-{(2-chlorophenyl)methyl}-2-propylthio- 1H-imidazol-5-yl]propionate (0.71 g, 1.94 mmol) in water (10 mL) and methanol (5 mL) was treated with potassium carbonate (0.51 g, 3.7 mmol). The reaction mixture was refluxed on a steam bath for 2 hours, the methanol was evaporated, the aqueous layer was washed with diethyl ether, cooled in ice, and adjusted to pH 3.4 with aqueous hydrochloric acid solution. The resulting gummy solid was extracted into methylene chloride, washed with water, dried, and concentrated. The residue was triturated with diethyl ether to give 2-[1-{(2-chlorophenyl)methyl}-2-propylthio-1H-imidazol- 5-yl]propionic acid; mp 170°–172° C.

EXAMPLE 2

2-[1-{(2-Chlorophenyl)methyl}-2-propylthio-1H-imidazol-5-yl]- 3-phenylpropionic Acid (i) diethyl [1-{(2-chlorophenyl)methyl}amino-2,2-diethoxy]ethylmalonate To a solution of diethyl ketomalonate (57.7 g, 0.33 mol) in dry toluene (800 mL) cooled in ice water was added portionwise triphenylphosphoranylidene acetaldehyde (100.8 g, 0.33 mol) over a period of one hour. The mixture was then stirred an additional hour. To the cold solution was added triethyl orthoformate (110 mL, 0.662 mol), p-toluenesulfonic acid hydrate (4 g) and 3A molecular sieves (30 g). The mixture was heated in a hot water bath at 60° C. for 2 hours, cooled and the suspension was filtered. The filtrate was concentrated, the residue was dissolved in 3:2 hexane/diethyl ether, and then chilled. The solid was separated, and the solution was concentrated to about 100 g of crude product which was flash chromatographed over 800 g of silica gel, eluting with 3:2 hexane/diethyl ether to give 87.14 g (96%) of diethyl 2,2-diethoxyethylidene malonate as a syrup.

This product (87.14 g, 0.318 mol) was dissolved in absolute ethanol (400 mL) and treated rapidly with a solution of 2-chlorobenzylamine (44.9 g, 0.318 mol) in ethanol (200 mL). The mixture was stirred for 4 hours at ambient temperature and then concentrated in vacuo to give 124.4 g of crude diethyl [1-{(2-chlorophenyl)methyl}- amino-2,2-diethoxy]ethylmalonate.

(ii) diethyl [1-{(2-chlorophenyl)methyl}-2-propylthio-1H-imidazol-5-yl]malonate

Ice cold 1N aqueous hydrochloric acid solution (126 mL) was treated with potassium thiocyanate (11.8 g, 0.121 mol). After 5 minutes, diethyl [1-{(2-chloro- phenyl)methyl/amino- 2,2-diethoxy]ethylmalonate (50 g, 0.12 mol) in ethanol (300 mL) was added rapidly, and the solution was heated on a steam bath for 6 hours. The ethanol was evaporated, the product was extracted into methylene chloride, dried, and concentrated to about 40 g of crude diethyl [1-{(2-chlorophenyl)methyl}- 2-thio-1H-imidazol-5-yl]malonate. This material was used as is for the next reaction.

A solution of this product (4.03 g, 0.0106 mol) in acetonitrile (100 mL) was treated with n-propylbromide (25 mL) and refluxed for 18 hours. The solvent was removed under vacuum to provide the syrupy, crude diethyl [1-{(2-chlorophenyl)methyl}-2-propylthio-1H-imidazol-5-yl]malonate (5.1 g, 97%).

(iii) diethyl [1-{(2-chlorophenyl)methyl}-2-propylthio-1H-imidazol-5-yl]phenyl-methylmalonate To a solution of sodium ethoxide (0.0596 g, 2.59 mmol) in absolute ethanol (10 mL) was added a solution of diethyl [1-{(2-chlorophenyl)methyl}-2-propylthio-1H-imidazol-5-yl]malonate (1.05 g, 2.47 mmol) in absolute ethanol (5 mL). This mixture was stirred under argon for 10 minutes, then benzyl bromide (0.309 mL, 2.59 mmol) was added. The reaction mixture was stirred at 25° C. for 30 minutes, then refluxed for 18 hours. The cooled mixture was partitioned between diethyl ether/water. The ethereal phase was washed with brine, dried with anhydrous sodium sulfate, and concentrated to 1.25 g of crude product which was flash chromatographed over silica gel with 85:15 methylene chloride/ethyl acetate to give 0.66 g (52%) of diethyl [1-{(2-chlorophenyl)methyl}-2-propylthio-1H-imidazol- 5-yl]-phenyl- methylmalonate as a syrup.

(iv) 2-[1-{(2-chlorophenyl)methyl}-2-propylthio-1H-imidazol- 5-yl]-3-phenyl-propionic acid A mixture of diethyl [1-{(2-chlorophenyl)methyl}-2-propylthio- 1H-imidazol-5-yl]phenylmethyl-malonate (0.66 g, 1.28 mmol), sodium carbonate (1.36 g, 1.28 mmol), ethanol (15 mL) and water (10 mL) was refluxed on a steam bath for 18 hours. The mixture was concentrated to a small volume, some insolubles were filtered, the aqueous layer was washed with diethyl ether and then the aqueous phase was adjusted to pH 3.4 with aqueous hydrochloric acid. The product was extracted into methylene chloride, washed with water, dried and concentrated to give 2-[1-{(2-chlorophenyl)methyl}-2-propylthio- 1H-imidazol-5-yl]-3-phenyl-propionic acid; mp 60°–63° C.

EXAMPLE 3

2-Carbethoxy-3-[1-{(2-chlorophenyl)methyl}-2-propylthio-1H-imidazol- 5-yl]propanoic Acid (i) 5-carboxymethyl-1-(2-chlorophenyl)methyl-2-thio-1H-imidazole A solution of 2-chlorobenzylamine (14.2 g, 0.1 mol) and triethylamine (13.9 mL, 0.1 mol), in dimethylformamide (100 mL) was treated with methyl chloroacetate (10.9 g, 0.1 mol), and the mixture was heated at 50° C. for 3.5 hours. The cooled reaction mixture was diluted with diethyl ether, the solids filtered and the concentrated filtrate was flash chromatographed over silica gel with 6:5 hexane in ethyl acetate to provide 15.3 g (71%) of homogenous methyl 2-[N-(2-chlorophenyl)methyl]aminoacetate. This product (15.2 g, 0.071 mol) in mixed xylenes (100 mL) was treated with 98% formic acid (2.74 mL, 0.0711 mol) and the mixture was refluxed for 2.5 hours with a Dean-Stark water separator. Evaporation gave 17.1 g (99%) of methyl 2-[N-(2-chlorophenyl)methyl-N-formyl)aminoacetate. This formylated product (17.0 g, 0.071 mol) was .dissolved in methyl formate (13.3 mL, 0.216 mol) and added dropwise to a sodium methoxide mixture prepared by adding sodium metal (1.79 g, 0.0778 g-atom) to tetrahydrofuran (325 mL) followed by slow addition of methanol (3.15 mL, 0.0778 mol). The combined mixture was stirred at room temperature for 18 hours, then evaporated to dryness. This crude product was dissolved in 50% aqueous methanol (200 mL), treated with charcoal, filtered and the solution was cooled in ice. Concentrated hydrochloric acid (14.3 mL of 12N, 0.171 mol) was added slowly to this solution followed by a solution of potassium thiocyanate (8.6 g, 0.0885 mol) in water (20 mL). The mixture was heated in an oil bath held at 90° C. for 2.5 hours, then cooled to −10° C. The precipitated solid was filtered, washed with cold ethanol-water and dried at 60° C. to provide 14.7 g (74%) of 5-carboxymethyl-1-(2-chlorophenyl)methyl-2-thio- 1H-imidazole; mp 72°–74° C.

(ii) 1-(2-chlorophenyl)methyl-5-carboxymethyl-2-propylthio- 1H-imidazole

A mixture of 5-carboxymethyl-1-(2-chlorophenyl)methyl-2-thio- 1H-imidazole (2 g, 7.08 mmol), ethyl acetate (20 mL), 5% sodium carbonate solution (40 mL) and propyl bromide (4 mL, 44 mmol) was heated at 60° C. for 18 hours. The organic layer was separated, dried over magnesium sulfate and concentrated to 2.23 g of crude product. Trituration with diethyl ether provided 1.63 g (71%) of 5-carboxymethyl-1-(2-chlorophenyl)methyl- 2-propylthio-1H-imidazole; mp 68°–71° C. (from hexane).

(iii) 1-(2-chlorophenyl)methyl-5-chloromethyl-2-propylthio- 1H-imidazole

A solution of 5-carboxymethyl-1-(2-chlorophenyl)methyl- 2-propylthio-1H-imidazole (3.74 g, 11.5 mmol) in dry tetrahydrofuran (50 mL) was cooled to −78° C. under argon, and a solution of diisobutyl aluminum hydride in toluene (30 mL of 1M) was added dropwise. The mixture was stirred at −78° C. for 1.5 hours, then allowed to slowly warm to room temperature. The reaction was quenched by pouring onto iced dilute acetic acid, the product was extracted into methylene chloride, and the organic extracts were washed with water, 5% sodium carbonate solution and brine. The dried, concentrated product was a light tan solid (3.32 g). Crystallization from ethanol/water gave 1-(2-chlorophenyl)methyl-5-hydroxymethyl- 2-propylthio-1H-imidazole; mp 98°–101° C.

A mixture of 1-(2-chlorophenyl)methyl-5-hydroxy-methyl- 2-thiopropyl-1H-imidazole (10 g, 0.0337 mol) in thionyl chloride (75 mL) was refluxed for one hour, evaporated in vacuo and the residue azeotroped three times with toluene. The solid was triturated with diethyl ether and collected to provide 10.4 g (88%) of the hydrochloride salt of 1-(2-chlorophenyl)methyl- 5-chloromethyl-2- propyl-thio-1H-imidazole.

(iv) diethyl [1-{(2-chlorophenyl)methyl}-2-propylthio-1H-imidazol-5-yl]methylmalonate To dry dimethylformamide (10 mL) under argon was added sodium hydride (0.14 g, 5.83 mmol) followed by diethyl malonate (0.92 g, 5.75 mmol) in dimethylformamide (2 mL) at 0° C. The mixture was stirred at ambient temperature for one hour. A solution of 5-chloromethyl-1-(2-chlorophenyl)methyl- 2-propylthio-1H-imidazole hydrochloride (1.0 g, 2.84 mmol) in dimethylformamide (4 mL) was added over 5 minutes. The reaction mixture was stirred at 25° C. for 18 hours, then partitioned between water and methylene chloride. The organic layer was washed with water, dried, and concentrated. The crude product was flash chromatographed over silica gel with 1:1 hexane/ethyl acetate to give 0.62 g (49.7%) of diethyl [1-{(2-chlorophenyl)methyl}-2-propylthio-1H-imidazol- 5-yl]methylmalonate as a pale yellow syrup.

(v) 2-carbethoxy-3-[1-{(2-chlorophenyl)methyl}-2-propylthio- 1H-imidazol-5-yl]-propanoic acid A solution of diethyl [1-{(2-chlorophenyl)methyl}-2-propylthio- 1H-imidazol-5-yl]methylmalonate (0.62 g, 1.41 mmol), sodium carbonate (1.5 g, 14.2 mol), ethanol (10 mL) and water (10 mL) was stirred at 25° C. for 18 hours, then heated for 15 minutes on a steam bath. The mixture was cooled, neutralized with aqueous hydrochloric acid solution, and the product was extracted into methylene chloride, washed with water, dried and concentrated to 0.425 g of product. Crystallization from ethyl acetate/hexane provided 0.23 g (55%) of 2-carbethoxy-3-[1-{(2-chlorophenyl)methyl}-2-propylthio- 1H-imidazol-5-yl]propanoic acid; mp 118°–120° C.

EXAMPLE 4

3-[1-{(2-Chlorophenyl)methyl}-2-propylthio-1H-imidazol-5-yl]propanoic Acid (i) ethyl [1-{(2-chlorophenyl)methyl}-2-propylthio-1H-imidazol- 5-yl propanoate.

Diethyl [1-{(2-chlorophenyl)methyl}-2-propylthio-1H-imidazol- 5-yl]-methylmalonate [Example 3(i)] (0.117 g, 0.285 mmol) was heated neat in air at 125°–130° C. for one hour. The title compound (0.14 g) was isolated as an oil.

(ii) 3-[1-{(2-chlorophenyl)methyl}-2-propylthio-1H-imidazol- 5-yl]propanoic acid A solution of the above ethyl ester (0.14 g, 0.382 mmol) in 50% aqueous ethanol (4 mL) and potassium hydroxide (0.075 g, 1.34 mmol) was stirred at 25° C. for 0.5 hours, water was added, and the mixture was neutralized with aqueous hydrochloric acid solution. A precipitate resulted. The solid was filtered, washed with water, dried and crystallized from ethanol to give 70 mg (54%) of 3-[1-{(2-chlorophenyl)methyl}-2-propylthio-1H-imidazol-5-yl]propanoic acid; mp 169°–170° C.

EXAMPLE 5

3-[2-n-Butyl-1-{(2-chlorphenyl)methyl}-1H-imidazol-5-yl]propanoic Acid (i) 2-n-butyl-1-(trimethylsilyl)ethoxymethyl-imidazole Hexane-washed 80% sodium hydride (1.45 g, 0.0483 mol) in dimethylformamide (80 mL) under argon was treated with a solution of 2-n-butylimidazole (5.45 g, 0.0439 mol) in dimethylformamide (14 mL) dropwise at 25° C., and the reaction was stirred an additional hour. Then, 2-(trimethylsilyl)ethoxymethyl chloride (SEM-Cl) (7.68 g, 0.0461 mol) was added, the mixture was stirred for 18 hours at ambient temperature and then partitioned between ice water and ethyl acetate. The washed, dried, concentrated organic solution was flash chromatographed over silica gel with 1:1 hexane in ethyl acetate to yield 10.8 g (96%) of 2-n-butyl-1-(trimethylsilyl)ethyoxymethyl-imidazole.

(ii) 2-n-butyl-5-tributyltin-1-(trimethylsilyl)-ethoxymethylimidazole

A solution of 2-n-butyl-1-SEM imidazole (prepared above) (6.37 g, 0.025 mol) in diethyl ether (125 mL) was treated dropwise with n-butyl lithium (0.0255 mol, 10.2 mL of 2.5M in hexane) under argon at room temperature. After being stirred for an additional 45 minutes, tributyltin chloride (8.83 g, 7.4 mL, 0.026 mol) was added dropwise. The suspension was stirred overnight, saturated ammonium chloride solution was added, and the ether layer was separated, washed with brine, dried over sodium sulfate, concentrated and flash chromatographed over silica gel with 3:1 hexane/ethyl acetate to provide 11.3 g (83%) of 2-n-butyl-5-tributyltin-1-(trimethylsilyl)ethoxy-methylimidazole.

(iii) ethyl (E and Z)-3-[2-n-butyl-1-{(trimethylsilyl)ethoxymethyl}- 1H-imidazol-5-yl]-2-propenoate To a solution of n-butyl-5-tributyltin-1-(trimethylsilyl)ethoxymethylimidazole (11.3 g, 0.0208 mol) in m-xylene (150 mL) was added ethyl 3-bromopropanoate (4.17 g, 0.0233 mol), followed by tetrakis (triphenyl-phosphine)-palladium(O) (0.48 g, 0. 416 mmol). The reaction mixture was heated at 120° C. for 18 hours under argon. The cooled mixture was washed with water, 10% ammonium hydroxide solution and brine. The solution was treated with charcoal and sodium sulfate, filtered, concentrated and flash chromatographed over silica gel with 9:1 hexane in ethyl acetate to give 1.96 g (27%) of ethyl (Z)-3-[2-n-butyl-1-{(trimethylsilyl)ethoxymethyl}- 1H-imidazol-5-yl]-2-propenoate as an oil. Further elution with 4:1 hexane acetate afforded the E-isomer (1.98 g, 27%) as an oil.

(iv) ethyl 3-[2-n-butyl-1-{(trimethylsilyl)ethoxymethyl}-1H-imidazol-5-yl]propanoate A suspension of ethyl (E and Z)-3-[2-n-butyl-1-{trimethylsilyl)ethoxymethyl}-1H-imidazol-5-yl]-2-propanoate (1.10 g, 3.12 mmol) in ethanol (25 mL) and 5% palladium on carbon (700 mg) was shaken on a Parr hydrogenation apparatus at 50 psi of hydrogen for 8.5 hours. The catalyst was filtered, and the filtrate was concentrated to 0.992 g (86%) of ethyl 3-[2-n-butyl-1-{(trimethylsilyl)ethoxymethyl}- 5-yl]-propanoate. TLC on silica gel with 7:3 hexane/ethyl acetate gave a single spot with an $R_f$ of 0.48.

(v) ethyl 3-[2-n-butyl-1-t-butoxycarbonyl-1H-imidazol-4-yl]propanoate

A solution of ethyl 3-[2-n-butyl-1-{(trimethylsilyl)ethoxymethyl}-1H-imidazol-5-yl]propanoate (0.992 g, 2.8 mmol) in ethanol (10 mL) was treated with 5N aqueous hydrochloric acid solution (20 mL), and then the reaction mixture was heated at 60° C. for 3.5 hours. The ethanol was evaporated, and the cooled aqueous solution was basified to pH 8 with 10% aqueous sodium hydroxide solution. The product was extracted into ethyl acetate, and the organic extracts were washed with brine, dried with anhydrous sodium sulfate and concentrated to give 0.314 g (50%) of ethyl 3-(2-n-butylimidazol- 4-yl)-propanoate. This was dissolved in methanol (15 mL) and di-tert-butyldicarbonate (2.44 g, 11.2 mmol) and triethylamine (1.56 mL, 11.2 mmol) were added. The mixture was stirred for 18 hours at ambient temperature, the solvent was evaporated, and the residue was dissolved in hexane and applied to a flash column packed with silica gel. Elution with 8:2 hexane/ethyl acetate afforded 0.285 g (31%) of ethyl 3-[2-n-butyl-1-t-butoxycarbonyl-1H-imidazol-4-yl]propanoate as an oil.

(vi) ethyl 3-[2-n-butyl-1-{(2-chlorophenyl)methyl}-1H-imidazol- 5-yl]propanoate

To a solution of trifluoromethanesulfonic anhydride (163 μL, 0.966 mmol) in methylene chloride (1 mL) held at −75° C. under argon was added 2-chlorobenzyl alcohol (138 mg, 0.966 mmol) and diisopropylethylamine (168 μL, 0.966 mmol) in methylene chloride (2 mL) over one minute. After being stirred for 15 minutes, a solution of ethyl 3-[2-n-butyl-1-t-butoxycarbonyl- 1H-imidazol-4-yl]propanoate (285 mg, 0.878 mmol) in methylene chloride (2 mL) was added over a 3-minute interval at −75° C. The reaction mixture was then allowed to warm to room temperature and was stirred for 18 hours. The solvent was evaporated, and this crude product was flash chromatographed over silica gel with a gradient of ethyl acetate in hexane to give 179 mg (58%) of ethyl 3-[2-n-butyl- 1-{(2-chlorophenyl)methyl}-1H-imidazol-5-yl]-propanoate as an oil. TLC on silica gel with 1:1 hexane/ethyl acetate showed a single product with an $R_f$ of 0.41.

(vii) 3-[2-n-butyl-1-{(2-chlorophenyl)methyl}-1H-imidazol- 5-yl]propanoic acid

A solution of ethyl 3-[2-n-butyl-1-{(2-chlorophenyl)methyl}-1H-imidazol-5-yl]propanoate (179 mg, 0.513 mmol) in ethanol (10 mL) was treated with sodium hydroxide (62 mg, 1.54 mmol) dissolved in water (2 mL). The solution was stirred for one hour at 25° C., cooled, acidified with 10% aqueous hydrochloric acid solution to pH 4.2 and concentrated to near dryness in vacuo. Water (3 mL) was added, and the resulting white solid was filtered, washed with water and dried to give 32 mg (20%) of 3-[2-n-butyl-1-{(2-chlorophenyl)methyl}-1H-imidazol-5-yl]propanoic acid; mp 163.5°–164.5° C.

EXAMPLE 6

3-[2-n-Butyl-1-{(2-chlorophenyl)methyl}-1H-imidazol-5-yl]butyric Acid (i) 2-n-butyl-1-(2-chlorophenyl)methyl-1H-imidazole Imidazole was converted to the 1-diethoxy-orthoamide derivative by the method of Curtis and Brown, *J. Org. Chem.*, 45, 20 (1980). Imidazole (12.8 g, 0.19 mol) and 118.4 g (0.8 mol) of triethylorthoformate were reacted in the presence of 1 g of p-toluenesulfonic acid to give 20.6 (61%), bp 65°–70° C. (0.1 mm) of 1-diethoxy-orthoamide imidazole. This product (24.0 g, 0.14 mol) was dissolved in dry tetrahydrofuran (250 mL), cooled to −40° C. and n-butyl lithium (0.14 mol, 56.4 mL of 2.5M in hexane) was added at −40° C. to −35° C. After 15 minutes, n-butyl iodide (31.1 g, 0.169 mol) was added at −40° C., and the reaction was stirred overnight at ambient temperature. The reaction was partitioned between diethyl ether and 0.3N hydrochloric acid, and the organic layer was repeatedly extracted with dilute hydrochloric acid. The combined aqueous extracts were neutralized with sodium bicarbonate solution, extracted with methylene chloride, dried over magnesium sulfate and concentrated. A flash distillation on a Kugelrohr apparatus provided 14.8 g (85%) of 2-n-butylimidazole.

2-n-Butylimidazole (9.7 g, 0.078 mol) was dissolved in methanol (50 mL) and added dropwise to a solution of sodium methoxide [from sodium hydride (2.31 g, 0.0934 mol) in methanol (250 mL)]. After one hour, the solution was evaporated to dryness, and the sodium salt was taken up in dry dimethylformamide (150 mL), and 2-chlorobenzyl bromide (16.3 g, 0.079 mol) was added. The mixture was heated at 50° C. for 17 hours under argon, poured onto ice water, and the product was extracted into ethyl acetate. The extract was washed, dried, and concentrated to give 18.5 g of crude product which was flash chromatographed over silica gel with 2:1 hexane/ethyl acetate to provide 11.9 g (61%) of 2-n-butyl- 1-(2-chlorophenyl)methyl-1H-imidazole as an oil. Thin layer chromatography on silica gel with 4:1 hexane/ethyl acetate gave an $R_f$ value of 0.59.

(ii) 2-n-butyl-1-(2-chlorophenyl)methyl-5-hydroxymethyl-1H-imidazole

Method A

A mixture of 2-n-butyl-1-(2-chlorophenyl)methyl-1H-imidazole (95.5 g, 0.384 mol), 37% formaldehyde (500 mL), sodium acetate (80 g) and acetic acid (60 mL) was heated to reflux for 40 hours under argon. The reaction was concentrated in vacuo, and the residue was stirred with 500 mL of 20% sodium hydroxide solution for 4 hours, diluted with water and extracted with methylene chloride. The extract was washed, dried, and concentrated. The crude product (117 g) was flash chromatographed over 600 g of silica gel with a gradient of ethyl acetate to 10% of methanol in ethyl acetate to give 8.3 g of starting material, 24.5 g of a mixture of starting material and product, and 44 g (41%) of 2-n-butyl-1-( 2-chlorophenyl)methyl-5-hydroxymethyl-1H-imidazole; mp 86°–88° C. (from ethyl acetate). Further elution provided the bis (4,5-hydroxymethyl) derivative; mp 138°–140° C. (from ethyl acetate).

Method B

A mixture of valeramidine methyl ether hydrochloride (250 g, 1.66 mol) and dihydroxyacetone (150 g, 0.83 mol) dissolved in liquid ammonia was allowed to stand overnight at room temperature in a pressure vessel, and then heated at 65° C. for 4 hours at 375 psi. The ammonia was allowed to evaporate, and the residue was dissolved in methanol (3 L). The resulting slurry was refluxed with added acetonitrile (1 L). The solution was decanted from the solid ammonium chloride while hot. This procedure was repeated, and the combined acetonitrile extracts were treated with charcoal, filtered hot, and the filtrate was concentrated in vacuo to give the dark oil, 2-n-butyl-5-hydroxymethylimidazole (253 g, 1.63 mol, 98%).

This crude alcohol (253 g) was treated with acetic anhydride (400 mL) at –15° C., and then was allowed to warm to ambient temperature with stirring, and then stirred an additional 19 hours. The acetic anhydride was evaporated at reduced pressure, the residue taken up in methylene chloride, and the organic phase was washed with 5% sodium bicarbonate solution and water. The extract was dried over sodium sulfate and concentrated to give 323 g (83%) of 1-acetyl-4-acetoxymethyl- 2-n-butylimidazole.

This diacetate was N-alkylated by the following procedure. To a solution of triflic anhydride (120 mL, 0.71 mol) in methylene chloride (200 mL) at –78° C. under argon was added a solution of diisopropyl ethylamine (128 mL, 0.73 mol) and 2-chlorobenzyl alcohol (104 g, 0.72 mol) in methylene chloride (350 mL) over a period of 20 minutes. After being stirred an additional 20 minutes at –78° C., this solution was then treated with 1-acetyl-4-acetoxymethyl-2-n-butylimidazole (146 g, 0.61 mol) dissolved in methylene chloride (300 mL) over a 20-minute interval. The mixture was then stirred at ambient temperature for 18 hours, and the solvents were evaporated.

The residual 2-n-butyl-5-acetoxymethyl-1-(2-chlorophenyl)methyl- 1H-imidazole was used without purification for the hydrolysis of the acetate group.

A solution of crude 2-n-butyl-5-acetoxymethyl-1-(2-chlorophenyl)methyl- 1H-imidazole (250 g) in methanol (200 mL) was treated with 10% sodium hydroxide solution (700 mL), and the mixture was heated on a steam bath for 4 hours. After cooling, methylene chloride was added, the organic phase was separated, washed with water, dried and concentrated. The residue was dissolved in ether, cooled, and seeded to give the crude product. Recrystallization from ethyl acetate gave 176 g of 2-n-butyl-1-(2-chlorophenyl)methyl-5-hydroxymethyl- 1H-imidazole; mp 86°–88° C. This material was identical in all respects to the product prepared by Method A.

(iii) 2-n-butyl-1-(2-chlorophenyl)methyl-1H-imidazol-5-carboxaldehyde

A solution of 2-n-butyl-1-(2-chlorophenyl)methyl-5-hydroxymethyl- 1H-imidazole (5.4 g, 0.0194 mol) in methylene chloride (25 mL) was added to a suspension of activated maganese dioxide (27 g) in methylene chloride (325 mL). The suspension was stirred at room temperature for 17 hours. The solids were filtered, and the filtrate concentrated and flash chromatographed over silica gel with 6:4 hexane/ethyl acetate to afford 4.16 g (78%) of 2-n-butyl-1-(2-chlorophenyl)methyl- 1H-imidazol-5-carboxaldehyde as an oil.

(iv) 2-n-butyl-1-(2-chlorophenyl)methyl-5-(a-hydroxy)-ethyl- 1H-imidazole

A solution of 2-n-butyl-1-(2-chlorophenyl)methyl-1H-imidazole- 5-carboxaldehyde (1.1 g, 3.97 mmol) was dissolved in dry tetrahydrofuran (15 mL), cooled to –78° C. under argon, and a solution of methyl lithium (3.64 mL of 1.2M in diethyl ether, 4.57 mmol) was added dropwise. The mixture was stirred for 1.5 hours, quenched with ammonium chloride solution, warmed to ambient temperature and extracted with ethyl acetate. The washed, dried, concentrated product was flash chromatographed over silica gel with ethyl acetate to provide 1.07 g (92%) of 2-n-butyl-1-(2-chlorophenyl)methyl-5-(a-hydroxy)ethyl- 1H-imidazole.

(v) [2-n-butyl-1-{(2-chlorophenyl)methyl}-1H-imidazol-5-yl]methyl ketone

A mixture of 2-n-butyl-1-(2-chlorophenyl)methyl-5-(a-hydroxy)ethyl- 1H-imidazole (1.07 g, 3.65 mmol), activated maganese dioxide (6 g) and toluene (75 mL) was heated at 90° to 100° C. under a slight vacuum with a Dean-Stark water separator for 17 hours. The inorganics were filtered, the concentrated filtrate was applied to a flash silica gel column, and the product was eluted with 3:7 hexane/ethyl acetate to give 0.628 g (59%) of [2-n-butyl-1-{(2-chlorophenyl)methyl}-1H-imidazol-5-yl]methyl ketone.

(vi) ethyl (E)-3-[2-n-butyl-1-{(2-chlorophenyl)methyl}-1H-imidazol-5-yl]-3-methyl-2-propenoate To absolute ethanol (3 mL) was added freshly cut sodium (55 mg). Then triethyl phosphonoacetate (0.504 g, 2.16 mmol) and [2-n-butyl-1-{(2-chlorophenyl)methyl}-1H-imidazol-5-yl]methyl ketone (0.628 g, 2.16 mmol) were added, and the mixture was stirred at 70° C. for 17 hours. The reaction was concentrated, partitioned between ethyl acetate and water, and the organic layer was washed with water, dried, concentrated and flash chromatographed to afford 214 mg (27%) of the title compound. The NMR was consistent with a trans relationship of imidazole to the carboxylate group.

(vii) methyl 3-[2-n-butyl-1-{(2-chlorophenyl)methyl}-1H-imidazol- 5-yl]butyrate

A mixture of methyl (E)-3-[2-n-butyl-1-{(2-chlorophenyl)methyl}-1H-imidazol-5-yl]-3-methyl-2-propenoate (165 mg, 0.476 mmol) in methanol (10 mL) and platinum oxide (20 mg) was shaken under one atmosphere of hydrogen for 3 hours. TLC on silica gel with 6:4 hexane/ethyl acetate showed a homogenous spot with an $R_f$ 0.54. The catalyst was filtered, and the filtrate was concentrated to 154 mg (93%) of the title compound.

(viii) 3-[2-n-butyl-1-{(2-chlorophenyl)methyl}-1H-imidazol- 5-yl]butyric acid

The procedure of Example 5 (vii) was followed using methyl 3-[2-n-butyl-1-{(2-chlorophenyl)methyl}-1H-imidazol-5-yl]butyrate in place of ethyl 3-[2-n-butyl-1-{(2-chlorophenyl)methyl}-1H-imidazol-5-yl]propanoate. The title compound is a white solid, obtained in 22% yield; mp 131°–133° C.

EXAMPLE 7

3-[1-{(2-Chlorophenyl)methyl}-2-propylthio-1H-imidazol-5-yl]- 2-benzylpropanoic Acid (i) Diethyl [1-{(2-chlorophenyl)methyl}-2-propylthio-1H-imidazol-5-yl]methyl-2-benzyl-malonate The procedure of Example 3(iv) was followed using diethylbenzylmalonate in place of diethylmalonate. From 2 g (5.7 mmol) of 5-chloromethyl-1-[(2-chlorophenyl)-methyl]-2-propylthio- 1H-imidazole hydrochloride and proportional amounts of other reagents, there was obtained, after silica gel chromatography with hexane/ethyl acetate, 2.23 g (74%) of diethyl [1-{(2-chlorophenyl)methyl}-2-propylthio-1H-imidazol-5-yl]methyl-2-benzylmalonate; mp 88°–89° C. (from hexane).

(ii) 3-[1-{(2-chlorophenyl)methyl}-2-propylthio-1H-imidazol- 5-yl]-2-benzyl-propanoic acid A mixture of diethyl [1-{ (2-chlorophenyl)methyl}-2-propylthio- 1H-imidazol-5-yl]methyl-2-benzyl-malonate (0.72 g, 1.36 mmol), potassium hydroxide (0.83 g, 14.7 mmol), water (15 mL) and ethanol (25 mL) was refluxed for 4 hours. The ethanol was evaporated, the residual aqueous layer was extracted with diethyl ether, and the basic solution was adjusted to pH 3.75 with concentrated hydrochloric acid. The precipitated product was extracted into methylene chloride, dried, and concentrated. This crude product was flash chromatographed on silica gel with 10% methanol in methylene chloride to give 0.51 g (86%) of 3-[1-{(2-chlorophenyl)methyl}-2-propylthio-1H-imidazol-5-yl]-2-benzylpropanoic acid; mp 123°–127° C.

EXAMPLE 8

3-[2-n-Butyl-1-{(2-chlorophenyl)methyl}-1H-imidazol-5-yl]-2-benzylpropanoic Acid (i) 2-n-butyl-1-(2-chlorophenyl)methyl-5-chloromethyl-1H-imidazole A mixture of 2-n-butyl-1-(2-chlorophenyl)methyl-5-hydroxymethyl- 1H-imidazole [Example 6(i)] (4.0 g) in thionyl chloride (80 mL) was refluxed for one hour, evaporated in vacuo, and the residue azeotroped three times with toluene. The solid was triturated with diethyl ether and collected to provide 3.5 g of the hydrochloride salt of 2-n-butyl- 1-(2-chlorophenyl)methyl-5-chloromethyl-1H-imidazole.

(ii) diethyl [2-n-butyl-1-{(2-chlorophenyl) methyl}-1H-imidazol- 5-yl]-2-benzyl-malonate The procedures of Example 3(iv) and Example 7 were followed. From 5.51 g (0.022 mol) of diethyl benzylmalonate, 0.53 g (0.022 mol) of sodium hydride, 50 mL of dimethylformamide and 3.5 g (0.0105 mol) of 2-n-butyl-1-(2-chlorophenyl)methyl- 5-chloromethyl-1H- imidazole hydrochloride, there was obtained 4.54 g (85%) of the title compound as an oil.

(iii) 3-[2-n-butyl-1-{(2-chlorophenyl)methyl}-1H-imidazol-5-yl]-2-benzylpropanoic acid The procedure of Example 7(ii) was followed using diethyl [2-n-butyl-1-{(2-chlorophenyl)methyl}-1H- imidazol-5-yl]-2-benzylmalonate in place of diethyl [1-{(2-chlorophenyl)methyl}-2-propylthio-1H- imidazol-5-yl]methyl-2-benzylmalonate. The title compound is a white solid; mp 118°–120° C. (from acetone/diethyl ether) as the hydrochloride salt.

EXAMPLE 9

Methyl 3-[2-n-Butyl-1-{(2-chlorophenyl)methyl}-1H-imidazol-5-yl] -2-benzylpropanoate A solution of 3-[2-n-butyl-1-{(2-chlorophenyl)methyl}-1H-imidazol-5-yl]-2-benzylpropanoic acid [Example 8] (0.5 g) was dissolved in methanol (100 mL) and treated with excess diethyl ether saturated with dry hydrochloric acid. The mixture was kept at 25° C. for 48 hours. The solvents were evaporated, the residue dissolved in a small amount of methanol. Crystallization was induced with diethyl ether. The solid was collected, washed with diethyl ether, and dried to afford 0.47 g (90%) of the title compound; mp 118.5°–120.5° C.

EXAMPLE 10

3-[2-n-Butyl-4-chloro-1-{(2-chlorophenyl)methyl}-1H-imidazol- 5-yl]-2-benzylpropanoic Acid (i) methyl 3-[2-n-butyl-4-chloro-1-{(2-chlorophenyl)methyl}-1H-imidazol-5-yl]-2-benzylpropanoate To a solution of methyl 3-[2-n-butyl-1-{(2-chlorophenyl)methyl}-1H-imidazol-5-yl]-2-benzylpropanoate [Example 9 (4.34 g, 0.01 mol) in tetrahydrofuran (20 mL) was added N-chlorosuccinimide (1.35 g, 0.01 mol) in portions over a one hour period. The mixture was heated to 60° C. for one-hour. The tetrahydrofuran was evaporated, the residue was dissolved in ethyl acetate and washed with 5% aqueous sodium bicarbonate solution and water. The dried, concentrated product was flash chromatographed over silica gel with 1:1 hexane/ethyl acetate to provide 2.7 g (55%) of the title compound.

(ii) 3-[2-n-butyl-4-chloro-1-{(2-chlorophenyl)methyl}-1H-imidazol-5-yl]-2-benzyl-propanoic acid The procedure of Example 4(ii) was followed using methyl 3-[2-n-butyl-4-chloro-1-{(2-chlorophenyl)methyl}-1H-imidazol- 5-yl]-2-benzylpropanoate in place of ethyl [1-{(2-chlorophenyl)methyl}-2-propylthio-1H-imidazol-5-yl]propanoate. The title compound is a white solid; mp 138°–139° C. (from acetonitrile).

EXAMPLE 11

3-[2-n-Butyl-1-benzyl-1H-imidazol-5-yl]-2-benzyl-propanoic Acid (i) methyl 3-[2-n-butyl-1-benzyl-1H-imidazol-5-yl]-2-benzylpropanoate A solution of methyl 3-[2-n-butyl-{(2-chlorophenyl)methyl}-1H-imidazol-5-yl]-2-benzylpropanoate [Example 9] (0.75 g) in methanol (25 mL) was stirred with platinum oxide (0.07 g) at room temperature under one atmosphere of hydrogen for 18 hours. Column chromatographic separation of the crude product over silica gel with 10% methanol in ethyl acetate gave 0.52 g of the crude de-chlorinated product. This was further purified on a prep silica gel plate using 30% acetone in hexane to provide 0.125 g of methyl 3-[2-n-butyl-1-benzyl- 1H-imidazol-5-yl]-2-benzylpropanoate as a syrup.

(ii) methyl 3-[2-n-butyl-1-benzyl-1H-imidazol- 5-yl]-2-benzylpropanoic acid

A mixture of methyl 3-[2-n-butyl-1-benzyl-1H-imidazol-5yl]-2-benzylpropanoate (0.12 g, 0.31 mmol) in 50% aqueous ethanol (4 mL) containing potassium hydroxide (0.072 g, 1.28 mmol) was stirred at 25° C. for 18 hours. The basic solution was diluted with water (8 mL), and extracted with diethyl ether. The water solution was acidified with aqueous hydrochloric acid solution to pH 4, and the product was extracted into methylene chloride, dried, and concentrated. This crude material was dissolved in acetone and acidified with ethereal hydrochloric acid to give a precipitate. Crystallization from acetone/ether provided 0.07 g of 3-[2-n-butyl- 1- benzyl-1H-imidazol-5-yl]-2-benzylpropanoic acid; mp 148°–150° C. (hydrochloride salt).

EXAMPLE 12

[2-n-Butyl-1-{(2-chlorophenyl)methyl}-1H-imidazol-5-yl]-2-benzylmalonic Acid A solution of diethyl [2-n-butyl-1-{(2-chlorophenyl)methyl}-1H-imidazol-5-yl]-2-benzyl-malonate [Example 8(iii)] (5.54 g, 0.0108 mol) in ethanol (75 mL) was treated all at once with a solution of potassium hydroxide (3.65 g, 0.065 mol) in water (50 mL). The resulting mixture was stirred at room temperature for 24 hours, then refluxed for 3 hours. The ethanol was evaporated, water was added to the aqueous product, and the basic solution was extracted with diethyl ether. The aqueous layer was acidified to pH 4 with hydrochloric acid and the product was extracted into ethyl acetate. The dried, concentrated product was crystallized twice from ethyl acetate to give 0.6 g of 2-n-butyl-1-{(2-chlorophenyl)methyl}-1H-imidazol-5-yl]-2-benzyl-malonic acid; mp 165°–166° C.(d). The filtrates from the crystallizations (4.9 g) consisted of additional malonic acid, the propanoic acid derivative and the mono ethyl ester malonate derivative. These are converted to [2-n-butyl-1-{(2-chlorophenyl)methyl}- 1H-imidazol-5-yl]-2-benzylpropanoic acid by the method described previously.

EXAMPLE 13

3-[{(2-Chlorophenyl)methyl}-2-propylthio-1H-imidazol-5-yl]-2-( 2-propenyl)propanoic Acid The procedure of Example 8 was followed using diethyl (2-propenyl)malonate in place of diethyl benzyl-malonate. From 2.8 g (0.014 mol) of diethyl (2-propenyl)-malonate, 2 g (0.0057 mol) of 5-chloromethyl-1-[(2-chlorophenyl)methyl]-2-propylthio- 1H-imidazole hydrochloride (Example 3) and proportional amounts of the other reagents, there was obtained, after heating the derived free malonic acid at 170° C. for 1 hour and flash chromatography over silica gel with 5% methanol in methylene chloride, 0.281 g of 3-[{(2-chlorophenyl)methyl} -2-propylthio-1H-imidazol-5-yl]-2-(2-propenyl)propanoic acid; mp 121°–122° C.

EXAMPLE 14

3-[2-n-Butyl-1-{(2-chlorophenyl)methyl}-1H-imidazol-5-yl]-2-n-butylpropanoic Acid (i) methyl 3-[2-n-butyl-1-{(2-chlorophenyl)methyl}-1H-imidazol- 5-yl]-2-n-butyl-propanoate A mixture of methyl (E and Z)-3-[2-n-butyl-1-{(2-chlorophenyl)methyl}-1H-imidazol-5-yl]-2-n-butyl-propenoate hydrochloride salt (prepared by the method in Example 6, replacing methyl lithium with butyl lithium) (245 mg, 0.578 mmol) in methanol (15 mL) and platinum oxide (30 mg) was stirred under an atmosphere of hydrogen for 0.5 hours. The catalyst was filtered, the filtrate was concentrated, and the residue was triturated with diethyl ether to afford 181 mg (74%) of methyl 3-[2-n-butyl-1-{(2-chlorophenyl)methyl}-1H-imidazol- 5-yl]-2-n-butylpropanoate hydrochloride; mp 123°–125° C.

(ii) 3-[2-n-butyl-1-{(2-chlorophenyl)methyl}-1H-imidazol-5-yl]-2-n-butylpropanoic acid A mixture of methyl 3-[2-n-butyl-1-{(2-chlorophenyl)methyl}-1H-imidazol-5-yl]-2-n-butyl-propanoate hydrochloride (181 mg, 0.423 mmol) in ethanol (10 mL) was stirred with 10% aqueous sodium hydroxide solution (2 mL) for 18 hours. The pH was adjusted to pH 1.5 and the product was extracted into methylene chloride, washed with water, dried over anhydrous sodium sulfate and concentrated to an oil. Trituration with diethyl ether and chilling gave a first crop of 25 mg of the hydrochloride salt of 3-[2-n-butyl-1-{(2-chlorophenyl)methyl}-1H-imidazol-5-yl]-2-n-butylpropanoic acid; mp 128°–130° C.

EXAMPLE 15

3-[1-{(2-Chlorophenyl)methyl}-2-propylthio-1H-imidazol-5-yl]- 2-n-pentylpropanoic Acid (i) diethyl[1-{(2-chlorophenyl)methyl}-2-propylthio-1H-imidazol- 5-yl]methyl-n-pentyl-malonate The procedure of Example 3(iv) was followed using diethyl n-pentylmalonate in place of diethyl malonate. The product was purified over silica gel with 10% ethyl acetate in hexane to provide the title compound as a syrup in 29.5% yield.

(ii) 3-[1-{(2-chlorophenyl)methyl}-2-propylthio-1H-imidazol- 5-yl]-2-n-pentyl-propanoic acid A solution of diethyl [1-{(2-chlorophenyl)methyl}-2-propylthio- 1H-imidazol-5-yl]-2-n-pentylmalonate (0.86 g, 1.69 mmol) in ethanol (20 mL) was stirred with a solution of potassium hydroxide (0.38 g, 6,8 mmol) at reflux for 12 hours. The mixture was diluted with water and extracted with diethyl ether. The aqueous layer was acidified with 10% aqueous hydrochloric acid solution and the product was extracted into ethyl acetate. The organic extract was dried and concentrated to give 0.68 g of predominately the free malonic acid intermediate. This was heated in an oil bath at 170° C. for one hour. The residue was flash chromatographed over silica gel eluting with 5% methanol in methylene chloride to afford 0.235 g (34%) of 3-[1-{(2-chlorophenyl)methyl}-2-propylthio-1H-imidazol-5-yl]-2-n-pentylpropanoic acid; mp 122°–124° C. (hydrochloride salt).

EXAMPLE 16

3-[2-n-Butyl-1-{(2-chlorophenyl)methyl}-1H-imidazol-5-yl]-2-n-pentylpropanoic Acid The title compound was prepared by the method described in Example 14 (i–ii); mp 124°–127° C. (hydrochloride salt).

EXAMPLE 17

4-[1-{(2-Chlorophenyl)methyl}-2-propylthio-1H-imidazol-5-yl]butyric Acid (i) 5-(2-chloro)ethyl-1-[(2-chlorophenyl)methyl]-2-propylthio-1-H-imidazole Diethyl [1-{(2-chlorophenyl)methyl}-2-propylthio-1H-imidazol- 5-yl]malonate was converted to 2-[1-{(2-chlorophenyl)methyl}-2-propylthio-1H-imidazol-5-yl]acetic acid by the method described in Example 15. The methyl ester was prepared in methanol/hydrochloric acid to give methyl 2-[1-{ (2-chlorophenyl)methyl}-2-propylthio-1H-imidazol-5-yl]acetate hydro-chloride; mp 158°–159° C.

A solution of methyl 2-[1-{(2-chlorophenyl)methyl}-2-propylthio- 1H-imidazol-5-yl]acetate (2.1 g, 6.2 mmol) in dry tetrahydrofuran (150 mL) was cooled to –78° C. for 1.5 hours and at ambient temperature for 18 hours. Methanol was added followed by 5% aqueous acetic acid. The mixture was concentrated in vacuo, the residue was extracted with methylene chloride, and the organic extract was washed with 5% aqueous sodium carbonate solution, dried, and concentrated to give 2.33 g of crude product. This was chromatographed over silica gel with ethyl acetate to give 1.6 g (84%) of 1-[(2-chlorophenyl)methyl]-5-(2-hydroxy)ethyl-2-propylthio- 1H-imidazole as an oil.

A mixture of 1-[(2-chlorophenyl)methyl]-5-(2-hydroxy)-ethyl- 2-propylthio-1H-imidazole (0.1 g) was stirred with thionyl chloride (1 mL) for 30 minutes at 25° C. and then refluxed for 15 minutes. The reaction was concentrated at reduced pressure and azeotroped several times with dry toluene. The residue was triturated with diethyl ether to give 80 mg (68%) of 5-(2-chloro)ethyl-1-[(2-chlorophenyl)methyl]-2-propylthio-1H-imidazole hydrochloride; mp 133°–134° C.

(ii) diethyl 2-[1-{(2-chlorophenyl)methyl}-2-propylthio-1H-imidazol-5-yl]ethylmalonate The procedure of Example 3(iv) was followed using 5-(2-chloro)ethyl-1-[(2-chlorophenyl)methyl]-2-propylthio-1H-imidazole hydrochloride in place of 5-chloromethyl-1-[(2-chlorophenyl)methyl]2-propylthio-1H-imidazole hydrochloride. The title compound was obtained in 71% yield after chromatography over silica gel with a gradient of ethyl acetate in methylene chloride.

(iii) 4[1-{(2-chlorophenyl/methyl-2-propylthio-1H-imidazol- 5-yl]butyric acid

The procedure of Example 15(ii) was followed using diethyl 2-[1-{(2-chlorophenyl)methyl-2-propylthio-1H-imidazol- 5-yl] ethylmalonate in place of diethyl [1-{(2 -chlorophenyl)methyl-2-propylthio-1H-imidazol-5-yl]methyl-n-pentylmalonate. The title compound is a white solid obtained in 64% yield; mp 98°–99° C. (from acetonitrile).

EXAMPLE 18

5-[2-n-Butyl-1-{(2-chlorophenyl)methyl-1H-imidazole-5-yl]pentanoic Acid (i) methyl 5-[2-n-butyl-1-{(2-chlorophenyl)methyl-1H-imidazol- 5-yl]pentanoate (E,E)-5-[2-n-butyl-1{(2-chlorophenyl)methyl-1H-imidazol- 5-yl]-2,4-pentadienoic acid (top 219°–220° C., prepared from 2-n-butyl- 1-(2-chlorophenyl)methyl-1H-imidazol-5-carboxaldehyde [Example 6 (iii)], triethyl 4-phosphonocrotonate, and sodium hydride in glyme, followed by base hydrolysis) was converted to the methyl ester hydrochloride with hydrochloric acid in methanol, and this diene methyl ester (0.12 g) was hydrogenated in methanol (20 mL) in the presence of platinum oxide (15 mg) and one atmosphere of hydrogen for one hour. The catalyst was filtered and the concentrated filtrate was chromatographed over silica gel with 3:1 ethyl acetate/hexane to provide 0.073 g (61%) of methyl 5-[2-n-butyl-1-{(2-chlorophenyl)methyl- 1H-imidazol-5-yl] pentanoate.

(ii)  5-[2-n-butyl-1-{(2-chlorophenyl)methyl1H-imidazol-5-yl]pentanoic acid

The precursor methyl ester was hydrolyzed to the free acid with aqueous base by the procedure of Example 5 (vii) to provide 5-[2-n-butyl-1-{(2-chlorophenyl)methyl-1H-imidazol-5-yl]pentanoic acid; mp 95°–97° C. (hydrochloride salt).

EXAMPLE 19

6-[2-n-Butyl-1-{(2-chlorophenyl)methyl}-1H-imidazol-5-yl]hexanoic Acid (i) 6-[2-n-butyl-1-{(2-chlorophenyl)methyl}-1H-imidazol- 5-yl]-4-hexenoic acid To a suspension of (4-carboxybutyl)triphenyl-phosphonium bromide (1.04 g, 2.35 mmol) in dry tetrahydrofuran (25 mL) at 0° C. under argon was added n-butyl lithium in hexane (1.8 mL of 2.5M, 4.6 mmol). The reaction mixture was stirred for 15 minutes at 0° C. and then a solution of 2-n-butyl-1-(2-chlorophenyl)methyl- 1H-imidazol-5-carboxaldehyde [Example 6 (iii)] (0.5 g, 1.81 mmol) in tetrahydrofuran (25 mL) was added dropwise. The mixture was stirred an additional hour at 0° C. and then at ambient temperature for 3 days. Water was added and the mixture was extracted with diethyl ether. The aqueous layer was acidified to pH 3 with aqueous hydrochloric acid solution. The product was extracted into ethyl acetate, washed with water, dried, concentrated, and chromatographed over silica gel eluting with 5–10% methanol in methylene chloride to give 0.24 g of 6-[2-n-butyl-1-{(2-chlorophenyl)methyl}-1H-imidazol-5-yl]-4-hexenoic acid.

(ii) 6-[2-n-butyl-1-{(2-chlorophenyl)methyl}-1H-imidazol-5-yl]hexanoic acid

6-[2-n-Butyl-1-{(2-chlorophenyl)methyl}-1H-imidazol-5-yl]-4-hexenoic acid was converted to the methyl ester with methanol and ethereal hydrochloric acid. This methyl ester (302 mg) in methanol was hydrogenated with platinum oxide (25 mg) at one atmosphere of hydrogen for 2 hours. The isolated crude reduced ester was chromatographed over silica gel with 3:1 ethyl acetate/hexane to provide 0.125 g of methyl 6-[2-n-butyl-1-{(2-chlorophenyl)methyl}-1H-imidazol-5-yl]hexanoate. Basic hydrolysis of this ester with potassium hydroxide as described in Example 11(ii) provided 6-[2-n-butyl- 1-{(2-chlorophenyl)methyl}-1H-imidazol-5-yl]-hexanoic acid hydrochloride; mp 144°–145° C. (from acetone).

EXAMPLE 20

(2RS,3SR)-3-[2-n-Butyl-1-{(2-chlorophenyl)methyl-1H-imidazol- 5-yl]-2-benzyl-3-methylpropanoic Acid (i) ethyl (2RS,3SR)-3-[2-n-butyl-1-{(2-chlorophenyl)methyl}-1H-imidazol-5-yl]2-benzyl-3-methylpropanoate A suspension of ethyl (E)-3-[2-n-butyl-1-t-butoxycarbonyl- 1H-imidazol-4-yl]-2-benzyl-3-methyl-2-propenoate (1.59 g, 3.73 mmol), prepared by the method described in Example 5 using ethyl 3-bromo-2-benzyl-2-propenoate in place of 3-bromopropenoate, in ethanol (25 mL) with 5% palladium on carbon was reduced on the Parr hydrogenation apparatus at 40 psi of hydrogen for 8 hours. The isolated crude product was flash chromatographed over silica gel with a gradient of 6:1 to 4:1 hexane in ethyl acetate to afford 1.36 g (85%) of ethyl (2RS,3SR)-3-methylpropanoate as an oil.

A solution of this ester (1.36 g, 3.17 mmol) in methylene chloride was added at −78° C. to a solution prepared by the addition at −78° C. under argon of 2-chlorobenzyl alcohol (0.559 g, 3.88 mmol) and di- isopropyl ethylamine (0.83 mL) to trifluoromethanesulfonic anhydride (0.64 mL) in methylene chloride (40 mL). The reaction was allowed to warm to ambient temperature and was stirred for an additional 22 hours. A solution of 5% aqueous sodium bicarbonate solution was added, and the layers were separated, washed, and dried. The crude product was chromatographed over silica gel with 7:3 hexane/ethyl acetate to yield 1.06 g (74%) of ethyl (2RS, 3SR)-3-[2-n-butyl-1-{(2-chlorophenyl)methyl-1H-imidazol-5-yl]-2-benzyl-3-methylpropanoate as an oil.

(ii) (2RS,3SR)-3-[2-n-butyl-1-{(2-chlorophenyl)methyl-1H-imidazol-5-yl]-2-benzyl-3-methylpropanoic acid A solution of the precursor ethyl ester (1.01 g, 2.23 mmol) was dissolved in ethanol (12 mL) and 10% aqueous sodium hydroxide solution was added. The mixture was refluxed for 24 hours, the ethanol was evaporated and the aqueous residue was acidified with aqueous hydrochloric acid solution to pH 4. The product was extracted into ethyl acetate, washed with water, dried, and concentrated. The crude material (898 mg) was dissolved in a small amount of ethyl acetate, diethyl ether was added and the chilled mixture deposited 423 mg (45%) of (2RS,3SR)-3-[2-n-butyl-1-{(2-chlorophenyl)methyl- 1H-imidazol-5-yl]-2-benzyl-3-methylpropanoic acid; mp 216°–218° C.

EXAMPLE 21

3-[2-n-Butyl-1{(4-carboxyphenyl)methyl}-1H-imidazol-5-yl]-2-( 2-thienylmethyl)propanoic Acid 2-n-Butyl-1-[(4-carbomethoxyphenyl)methyl]-1H-imidazol- 5-carboxyaldehyde (6.07 g, 0.202 mol) dissolved in 50 mL of methanol was treated portionwise with 0.483 g (0.0128 mol) of sodium borohydride. After several minutes the pH of this mixture was brought to 7 with 10% aqueous hydrochloric acid solution, concentrated under vacuum, and water added. The resulting crystals were collected by filtration, washed with water, and dried to give 5.90 g (98%) of the corresponding alcohol, mp 141°–143° C. Thionyl chloride (7.5 mL) was added to 1.51 g (0.00499 mol) of the alcohol and the mixture heated on a steam bath for 45 minutes. Concentration under vacuum gave a syrup which was treated with 30 mL of ether and the ether removed under vacuum. Repetition of the ether-evaporation cycle times gave a solid which was taken up in 10 mL of methylene chloride and the solution added to ether to give 1.76 g (99%) of the chloromethyl imidazole hydrochloride, mp 151°–153° C.

Diethyl 2-thienyl-methylmalonate (2.68 g, 0.1245 mol) was added dropwise to a stirred suspension of 0.245 g (0.0102 mol) of sodium hydride in 25 mL of anhydrous dimethylformamide at ambient temperature under argon. After 2 hours a solution of 1.76 g (0.006 mol) of the chloromethyl imidazole hydrochloride in 10 mL of dry dimethylformamide was added and the mixture stirred 18 hours. The precipitated salt was removed by filtration and washed with ether. The combined filtrates were extracted four times with 25 mL portions of 6N aqueous hydrochloric acid solution, the aqueous treated with 50% sodium hydroxide to bring the pH to 9.5 and then extracted with ether. Concentration of the dried ether under vacuum gave 2.28 g (84%) of the triester as a syrup.

A mixture of 1.03 g (0.019 mol) of the triester and 25 mL of 12N hydrochloric acid was refluxed for 24 hours. The reaction mixture was concentrated to dryness under vacuum and triturated with ether to give 0.88 g of product as the hydrochloride. This was dissolved in water, the solution brought to pH 10 with 10% aqueous sodium hydroxide solution, filtered, and the pH brought to 4 with 6N hydrochloric acid. The solid which formed was collected by filtration, washed with water, and dried to give 0.53 g (65%) of the title compound; mp 175° C., softens 125° C.

EXAMPLE 22

3-[2-n-Butyl-1-{4-carboxyphenyl)methyl}-4-chloro]-1H-imidazol- 5-yl]-2-(2-thienylmethyl)-propanoic Acid The title compound was prepared following the procedure of Example 21 using 2-n-butyl-1-[(4-carbomethoxyphenyl)methyl]-4-chloro]-1H-imidazol-5-carboxaldehyde; mp 112°–115° C.

EXAMPLE 23

3-[2-n-Butyl-1-{(4-carboxyphenyl)methyl}-1H-imidazol-5-yl]-2-benzylpropanoic Acid The title compound was prepared following the procedure of Example 21 using 2-n-butyl-1-[(4-carbomethoxyphenyl)methyl]-1H-imidazol-5-carboxaldehyde and diethyl benzylmalonate; mp 120°–124° C.

EXAMPLE 24

3-[2-n-Butyl-1-{4-carboxyphenyl)methyl}-1H-imidazol-5-yl]-2-( 4-chlorobenzyl) propanoic Acid A mixture of 2-n-butyl-1-[(4-carbomethoxyphenyl)methyl]- 1H-imidazol-5-carboxaldehyde (5.0 g, 0.0167 mol), diethyl malonate (2.85 g, 0.0178 mol), piperidine (0.22 mL) and benzoic acid (4.3 mg) in 40 mL of benzene was refluxed under argon for 25 hours using a Dean-Stark trap to remove water. The mixture was washed in turn with saturated aqueous sodium bicarbonate, water, and saturated brine, and then concentrated under vacuum to give 7.93 g of a syrup. Flash chromatography on silica gel of 23.37 g of syrup eluting with 1:1 ethyl acetate-hexane gave 18.86 g of pure diester as an oil.

Sodium borohydride (0.80 g, 0.211 mol) was added in portions to a stirred solution of 17.86 g (0.040 mol) of diester in 50 mL of ethanol cooled in an ice bath. Addition of 10% aqueous hydrochloric acid solution to bring the pH to 7 was followed by evaporation to dryness under vacuum, partition of the residue between ether and water, and extraction of the aqueous layer with fresh ether. The combined ether extracts were washed in turn with water and brine, dried, and concentrated under vacuum to give 17.86 g (99%) of malonate as a syrup.

A solution of 1.37 g (0.00308 mol) of the malonate in 10 mL of dimethylformamide was added to a stirred suspension of 0.080 g (0.0034 mol) of sodium hydride in 10 mL of dry dimethylformamide under argon. After stirring the mixtures for one hour 0.54 g (0.0034 mol) of 4-chlorobenzylchloride in 5 mL of dimethylformamide was added and the stirring continued for 7 hours. The mixture was then poured into 150 mL of water and extracted 3 times with 400 mL of ether. The ether extract was washed with water and then brine, and concentrated under vacuum to give 1.64 g (94%) of the 4-chlorobenzyl malonate as a syrup. Flash chromatography on silica gel (7:3 ethyl acetate-hexane) gave 1.25 g (71%) of purified product as an oil. This was dissolved in a solution of 0.97 g of sodium hydroxide in 40 mL of 1:1 ethanol-water and stirred for 18 hours. The mixture was then heated on a steam bath for 1 hr to remove most of the ethanol, diluted with 20 mL of water, filtered, and the pH adjusted to 3.4 with 10% hydrochloric acid. The resulting solid was collected by filtration and washed to give 1.04 g of a solid; mp 119° C.; sublimed, mp 210° C. The product was refluxed in 30 mL of 12N hydrochloric acid for 18 hours and this mixture evaporated to give a foam. This was dissolved in ethanol, filtered, and concentrated under vacuum to a foam. This process was repeated to give 0.89 g (81%) of crystals of final product; mp 151°–156° C. (ethanol-ethyl acetate).

EXAMPLE 25

3-[2-n-Butyl-1-[(4-carboxyphenyl)methyl]-1H-imidazol-5-yl]-2-(4-methoxybenzyl)propanoic Acid The title compound was prepared following the procedure of Example 24 using 4-methoxybenzylchloride.

EXAMPLE 26

The following compounds are prepared using the procedures hereinbefore described:

3-[2-n-butyl-1-{(4-carboxy-2-chlorophenyl)methyl}-1H-imidazol- 5-yl]-2-benzylpropanoic acid, 3-[2-n-butyl-1-{(4-carboxy-3-chlorophenyl)methyl}-1H-imidazol- 5-yl]-2-benzylpropanoic acid, 3-[2-n-butyl-1-{(4-carboxy-2,3-dichlorophenyl)methyl}-1H-imidazol-5-yl]-2-benzylpropanoic acid, 3-[2-n-propyl-1-{(4-carboxyphenyl)methyl)-1H-imidazol-5-yl]-2-benzylpropanoic acid, 3-[2-n-hexyl-1-{(4-carboxyphenyl)methyl}-1H-imidazol-5-yl]-2-benzylpropanoic acid, 3-[2-n-butyl-1-{(4-carboxyphenyl)methyl}-1H-imidazol- 5-yl]-2-(3-thienylmethyl)propanoic acid, 3-[2-n-butyl-1-{(4-carboxyphenyl)methyl}-1H-imidazol-5-yl] -2-(2-furylmethyl)propanoic acid, and 3-[2-n-butyl-1-{(2-chlorophenyl)methyl}-1H-imidazol-5-yl]-2-(2-thienylmethyl)propanoic acid.

EXAMPLE 27

An oral dosage form for administering orally active Formula (I) compounds is produced by screening, mixing and filling into hard gelatin capsules the ingredients in proportions, for example, as shown below.

| Ingredients | Amounts |
|---|---|
| 3-[2-n-butyl-1-{(2-chlorophenyl)methyl}-1H-imidazol-5-yl]-2-benzylpropanoic acid | 100 mg |
| magnesium stearate | 10 mg |
| lactose | 100 mg |

EXAMPLE 28

The sucrose calcium sulfate dihydrate and orally active Formula (I) compounds are mixed and granulated with a 10% gelatin solution. The wet granules are screened, dried, mixed with the starch, talc and stearic acid, screened and compressed into a tablet.

| Ingredients | Amounts |
|---|---|
| 2-n-butyl-1-{(2-chlorophenyl)methyl 1H-imidazol-5-yl]-2-n-butylpropanoi acid | 75 mg |
| calcium sulfate dehydrate | 100 mg |
| sucrose | 15 mg |
| starch | 8 mg |
| talc | 4 mg |
| stearic acid | 2 mg |

EXAMPLE 29

3-[2-n-Butyl-1-{(chlorophenyl)methyl}-1H-imidazol-5-yl]-2-benzylpropanoic acid, 50 mg, is dispersed in 25 mL of normal saline to prepare an injectable preparation.

EXAMPLE 30

A topical ophthalmological solution for administering Formula (I) compounds is produced by mixing under sterile conditions the ingredients in proportions, for example, as shown below.

| Ingredients | Amounts (mg/mL) |
|---|---|
| 2-n-butyl-1-{(2-chlorophenyl)methy 1H-imidazol-5-yl]-2-n-butylpropano acid | 1.0 |
| dibasic sodium phosphate | 10.4 |
| monobasic sodium phosphate | 2.4 |
| chlorobutanol | 5.0 |
| hydroxypropanol methylcellulose | 5.0 |
| sterile water | q.s. ad 1.0 ml |
| 1.0N sodium hydroxide | q.s. ad pH 7.4 |

It is to be understood that the invention is not limited to the embodiments illustrated hereabove, and the right to the illustrated embodiments and all modifications coming within the scope of the following claims is reserved.

What is claimed is:

1. A method of antagonizing angiotensin II receptors in mammals which comprises administering to a subject in need thereof an effective amount of a compound of formula (I):

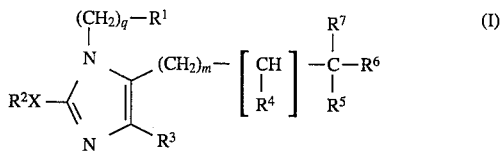

in which:

R$^1$ is adamanthylmethyl, or phenyl, biphenyl, or naphthyl, with each aryl group being unsubstituted or substituted by one to three substituents selected from Cl, Br, F, I, C$_{1-6}$alkyl, nitro, CO$_2$R$^8$, tetrazol-5-yl, C$_{1-6}$alkoxy, hydroxy, SC$_{1-4}$alkyl, SO$_2$ NHR$^8$, NHSO$_2$R$^8$, SO$_3$H, CONR$^8$R$^8$, CN, SO$_2$C$_{1-4}$alkyl, or C$_n$F$_{2n+1}$, wherein n is 1–3;

R$^2$ is C$_{2-10}$alkyl, C$_{3-10}$alkenyl, C$_{3-10}$alkynyl, C$_{3-6}$cycloalkyl, or (CH$_2$)$_{0-8}$phenyl unsubstituted or substituted by one to three substituents selected from C$_{1-6}$alkyl, nitro, Cl, Br, F, I, hydroxy, C$_{1-6}$alkoxy, NR$^8$R$^8$, CO$_2$R$^8$, CN, or CONR$^8$ R$^8$;

X is a single bond, S, or O;

R$^3$ is hydrogen, Cl, Br, F, I, CHO, hydroxymethyl, CO$_2$R$^8$, NO$_2$, or C$_n$F$_{2n+1}$, wherein n is 1–3;

q is 0 to 4;

m is 0 to 2;

R$^4$ is H or C$_{1-6}$alkyl;

z is 0 to 1;

R$^5$ is C$_{3-6}$alkenyl, phenyl-Y-, 2- or 3-thienyl-Y-, 2- or 3-furyl-Y-, 2-, 3-, or 4-pyridyl-Y-, tetrazolyl-Y-, triazolyl-Y-, imidazolyl-Y-, pyrazolyl-Y-, thiazolylo-Y-, pyrrolyl-Y-, or oxazolyl-Y-, with each aryl ring being unsubstituted or substituted by C$_{1-6}$alkyl, Cl, Br, F, I, C$_{1-6}$alkoxy, NR$^8$R$^8$, CO$_2$R$^8$, or CONR$^8$R$^8$;

Y is a single bond or C$_{1-6}$alkyl which is branched or unbranched;

R$^6$ is CO$_2$R$^8$, CONR$^8$R$^8$, or tetrazol-5-yl;

R$^7$ is H, CO R$^8$, or C$_{1-6}$alkyl; and each R$^8$ independently is hydrogen, C$_{1-6}$alkyl, or (CH$_3$)$_{0-4}$ phenyl; or a pharmaceutically acceptable salt thereof.

2. A method of claim 1 wherein the compound is 3-[2-n-butyl- 1-{(4-carboxyphenyl)methyl}-1H-imidazol-5-yl]-2-benzylpropanoic acid or a pharmaceutically acceptable salt thereof.

3. A method of claim 1 wherein the compound is 3-[2-n-butyl- 1-{(4-carboxyphenyl)methyl}1H-imidazol-5-yl]-2-(2-thienylmethyl)propanoic acid; or a pharmaceutically acceptable salt thereof.

4. A method of claim 1 wherein the compound is:

3-[2-n-butyl-1-{(2-chlorophenyl)methyl}-1H-imidazol-5-yl]-2-benzylpropanoic acid;

3-[2-n-butyl-1-{(2-chlorophenyl)methyl}-1H-imidazol-5-yl]-2-n-butylpropanoic acid;

3-[2-n-butyl-1-{(4-carboxyphenyl)methyl}-1H-imidazol-5-yl]-2-(4-chlorobenzyl)propanoic acid;

3-[2-n-butyl-1-{4-carboxyphenyl)methyl}-4-chloro-1H-imidazol- 5-yl]-2-(2-thienylmethyl)propanoic acid;

3-[2-n-butyl-4-chloro-1-{(2-chlorophenyl)methyl}-1H-imidazol- 5-yl]-2-benzylpropanoic acid;

(2RS,3SR)-3-[2-n-butyl-1-{(2-chlorophenyl)methyl}-1H-imidazol- 5-yl]-2-benzyl-3-methylpropanoic acid;

3-[2-n-butyl-1-benzyl-1H-imidazol-5-yl]-2-benzylpropanoic acid;

2-carboethoxy-3-[1-{(2-chlorophenyl)methyl}-2-propylthio- 1H-imidazol-5-yl]propanoic acid;

3-[1-{(2-chlorophenyl)methyl}-2-propylthio-1H-imidazol-5-yl]-2-benzylpropanoic acid;

3-[1-{(2-chlorophenyl)methyl}-2-propylthio-1H-imidazol-5-yl]-2-n-pentylpropanoic acid;

3-[1-{(2-chlorophenyl)methyl}-2-propylthio-1H-imidazol-5-yl]-2-(2-propenyl)propionic acid;

2-[2-n-butyl-1-{(2-chlorophenyl)methyl}-1H-imidazol-5-yl]-2-benzylmalonic acid; or methyl 3-[2-n-butyl-1-{(2-chlorophenyl)methyl}-1H-imidazol- 5-yl]-2-benzylpropionate.

5. A method of treating congestive heart failure in mammals which comprises administering to a subject in need thereof an effective amount of a compound of formula (I) as defined in claim 1.

6. A method of treating renal failure in mammals which comprises administering to a subject in need thereof an effective amount of a compound of formula (I) as described in claim 1.

7. A method of treating glaucoma in mammals which comprises administering to a subject in need thereof an effective amount of a compound of formula (I) as described in claim 1.

* * * * *

UNITED STATES PATENT AND TRADEMARK OFFICE
CERTIFICATE OF CORRECTION

PATENT NO. : 5,530,017
DATED : June 25, 1996
INVENTOR(S) : Girard, et al

It is certified that error appears in the above-indentified patent and that said Letters Patent is hereby corrected as shown below:

In claim 1, column 37, line 35, replace "$R^7$ is H, $COR^8$" with -- $R^7$ is H, $CO_2R^8$ --.

Signed and Sealed this

Seventeenth Day of September, 1996

Attest:

BRUCE LEHMAN

Attesting Officer    Commissioner of Patents and Trademarks